(12) United States Patent
Pareek et al.

(10) Patent No.: US 9,234,189 B2
(45) Date of Patent: Jan. 12, 2016

(54) HYBRID TYPE HISTIDINE KINASE GENE ISOLATED FROM INDICA RICE IR64

(75) Inventors: Ashwani Pareek, New Delhi (IN); Ratna Karan, New Delhi (IN); Gautam Kumar Roy, New Delhi (IN); Sneh Lata Singla-Pareek, New Delhi (IN)

(73) Assignee: Ashwani Pareek, New Delhi (IN)

( * ) Notice: Subject to any disclaimer, the term of this patent is extended or adjusted under 35 U.S.C. 154(b) by 787 days.

(21) Appl. No.: 13/058,741

(22) PCT Filed: Aug. 10, 2009

(86) PCT No.: PCT/IN2009/000444
§ 371 (c)(1),
(2), (4) Date: Feb. 11, 2011

(87) PCT Pub. No.: WO2010/018598
PCT Pub. Date: Feb. 18, 2010

(65) Prior Publication Data
US 2011/0239326 A1    Sep. 29, 2011

(30) Foreign Application Priority Data
Aug. 11, 2008  (IN) .......................... 1896/DEL/2008

(51) Int. Cl.
*C12N 9/12* (2006.01)
*C12N 15/82* (2006.01)

(52) U.S. Cl.
CPC .......... *C12N 9/1205* (2013.01); *C12N 15/8271* (2013.01)

(58) Field of Classification Search
USPC .......................... 800/278; 536/23.2; 435/91.2
See application file for complete search history.

(56) References Cited

U.S. PATENT DOCUMENTS

| | | | |
|---|---|---|---|
| 5,175,155 A | 12/1992 | Juniewicz et al. | |
| 5,488,075 A | 1/1996 | Guha | |
| 6,090,409 A | 7/2000 | Weisman et al. | |
| 2004/0123343 A1 | 6/2004 | La Rosa et al. | |
| 2007/0192889 A1* | 8/2007 | La Rosa et al. | 800/278 |

FOREIGN PATENT DOCUMENTS

| | | |
|---|---|---|
| WO | 02/099079 A2 | 12/2002 |
| WO | 2008/047834 A1 | 4/2008 |

OTHER PUBLICATIONS

Pareek et al. Whole-genome analysis of Oryza sativa reveals similar architecture of two-component signaling machinery with Arabidopsis. Plant Physiology. 2006. 142: 380-397.*
GenBank Accession No. DQ248962.1—Oryza sative (Indica cultivar group) hybrid type histidine kinase mRNA (GI: 82466314, submitted by Kumar et al. Oct. 17, 2005, retrieved from http://www.ncbi.nlm.nih.gov/nuccore/DQ248962 on Feb. 23, 2014.*
Furukawa K, Katsuno Y, Urao T, Yabe T, Yamada-Okabe T, Yamada-Okabe H, Yamagata Y, Abe K, Nakajima T. Isolation and functional analysis of a gene, tcsB, encoding a transmembrane hybrid-type histidine kinase from Aspergillus nidulans. Appl Environ Microbiol. Nov. 2002;68(11):5304-10.*
Tyagi W, Rajagopal D, Singla-Pareek SL, Reddy MK, Sopory SK. Cloning and regulation of a stress-regulated Pennisetum glaucum vacuolar ATPase c gene and characterization of its promoter that is expressed in shoot hairs and floral organs. Plant Cell Physiol. Aug. 2005;46(8):1411-22. Epub Jun. 15, 2005.*
Du L, Jiao F, Chu J, Jin G, Chen M, Wu P. The two-component signal system in rice (*Oryza sativa* L.): a genome-wide study of cytokinin signal perception and transduction. Genomics. Jun. 2007; 89(6):697-707. Epub Apr. 6, 2007.*
Pareek A, Singh A, Kumar M, Kushwaha HR, Lynn AM, Singla-Pareek SL. Whole-genome analysis of Oryza sativa reveals similar architecture of two-component signaling machinery with Arabidopsis. Plant Physiol. Oct. 2006; 142(2):380-97. Epub Aug. 4, 2006.*
Nongpiur R, Soni P, Karan R, Singla-Pareek SL, Pareek A. Histidine kinases in plants: cross talk between hormone and stress responses. Plant Signal Behav. Oct. 1, 2012; 7(10):1230-7. Epub Aug. 20, 2012. Review.*
Singla-Pareek SL, Yadav SK, Pareek A, Reddy MK, Sopory SK. Enhancing salt tolerance in a crop plant by overexpression of glyoxalase II. Transgenic Res. Apr. 2008; 17(2):171-80. Epub Mar. 27, 2007.*
Singh AK, Ansari MW, Pareek A, Singla-Pareek SL. Raising salinity tolerant rice: recent progress and future perspectives. Physiol Mol Biol Plants. Apr. 2008; 14(1-2):137-54. Epub Jun. 15, 2008.*
Uhlen et al. (1993). Affinity separation of Nucleic Acids on Monosized Magnetic beads, Chapter 31 from Molecular Interactions in Bioseparations published by Springer Science and edited by T. T Ngo, p. 479-485.*
Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*

(Continued)

*Primary Examiner* — Angela M Bertagna
*Assistant Examiner* — Olayinka Oyeyemi
(74) *Attorney, Agent, or Firm* — Conley Rose, P.C.; Rodney B. Carroll

(57) ABSTRACT

The present invention provides a hybrid-type histidine kinase gene isolated from indica rice IR64, and being capable of osmosensing and inducible by multiple stresses, and hence, being capable of improving the multiple stress tolerance of the crop plants even in subsequent generations so as to make the plants capable of coping-up with the more than one environmental abiotic stress conditions, and therefore, increasing the economic value of the crop plants while maintaining the yield thereof. The present invention also provides a method of isolation of hybrid-type histidine kinase gene from indica rice IR64, and its functional characteristics and its sequence listing and cloning, at least, with yeast expression vector and the plant expression vector, and clones produced thereby, and method of improving multiple stress tolerance of crop plant and crop plants having improved multiple stress tolerance.

9 Claims, 11 Drawing Sheets

(56) References Cited

OTHER PUBLICATIONS

Noriyuki Ochiai, et al; "Involvement of the osmosensor histidine kinase and osmotic stress-activated protein kinases in the regulation of secondary metabolism in *Fusarium graminearum*", Biochemical and Biophysical Research, 2007, vol. 363, No. 3, pp. 639-644 the whole document.

International Search Report: OCT/IN2009/000444, mailed Dec. 3, 2009.

Foreign communication from a related counterpart application—Supplementary Search Report, European Application No. 09806540.2, Mar. 2, 2012, 11 pages.

Foreign communication from a related counterpart application—Examination Report, European Application No. 09806540.2, May 19, 2014, 6 pages.

Foreign communication from a related counterpart application—Examination Report, European Application No. 09806540.2, Dec. 6, 2012, 5 pages.

Kumar, M., et al., "A hybrid type histidine kinase isoform a. *Oryza sativa* subsp. *indica*," XP002669706, Database UniProt [Online], retrieved from ebi, database accession No. Q2Q1D4, Jan. 24, 2006, 1 page.

Kumar, M., et al., "Oryza sativa indica group hybrid type histidine kinase isoform a mRNA," XP002669707, Database EMBL [Online], retrieved from ebi, database accession No. DQ248962, Jan. 1, 2006, 2 pages.

Sasaki, T., et al., "Putative histidine kinase 2. *Oryza sativa* susp *japonica*," XP002669708, Database UniProt [Online], retrieved from ebi, database accession No. Q5JJP1, Feb. 15, 2005, 2 pages.

Ueguchi, Chiharu, et al., "Novel Family of Sensor Histidine Kinase Genes in Arabidopsis thaliana," XP001079007, Plant Cell Physiol., 2001, pp. 231-235, vol. 42, No. 2, JSPP.

Urao, Takeshi, et al., "A Transmembrane Hybrid-Type Histidine Kinase in Arabidopsis Functions as an Osmosensor," XP002952931, The Plant Cell, Sep. 1999, pp. 1743-1754, vol. 11, American Society of Plant Physiologists.

\* cited by examiner

| Primers Name | Primers Sequences | |
|---|---|---|
| OsHk3bF | 5'ATGACGTTCGCGAGGTACGC3' | (SEQ ID NO:1) |
| OsHk3bR | 5'CTATTCAACTTGGTCATGATTTTG3' | (SEQ ID NO:2) |

| Steps | Temperature | Time | Number of Cycles |
|---|---|---|---|
| Initial denaturation | 94°C | 5 min | 1 |
| Denaturation | 94°C | 1 min | 34 |
| Annealing | 55°C | 1 min | |
| Extension | 72°C | 3 min | |
| Final extension | 72°C | 7 min | 1 |

```
ATGACGTTCGCGAGGTACGCGGTGAGGACGGCGTTCGAGCGGCCGCTGACGAGCGG
GGTGGCGTACGCGGTGCGGGTGACGCACGGCGAGCGGGAGCATTTCGAGCGGCAGC
AGGGGTGGACGATCAAGAAGATGTACTCCTCCTCCAACAAGAAGCAGTCGTCGTCG
GGGCCGGGGCCGGGGGACGCCGCCGTCGCGGAGATCCGGGAGCCCGCCGAGGAGTA
CGCCCCGGTCATCTTCGCCCAGGACGCCTACAAGCACGTCATCTCCTTCGACATGCTC
TCCGGGAATGAGGATCGGAAAAACATACTATACTCTAGGAAATCTGGCAAGGGTGT
GCTGACTGCTCCTTTCAAGCTACTGAATAATCGCCTCGGAGTAATCTCGACATACACT
GTTTATAAGTCTGAGCTCCCTGCAAATGCCAGGCCACATGAACGCATCCAAGCCGCG
ATTGGCTATTTGGGCGGCATATTTGACATACAAGCACTCGTCGAAAAGTTGCTCAAA
CAACTCGCGAGCCAGGAATCCATCATGGTGAATGTGTATGATACGACCAACGAGAA
CCCGATCAGTATGTACGGTGATGATACTGGGAGTGGCATGTGCCATGTCAGCGTGCT
CAACTTTGGTGATCCATCGAGAAAGCATGAGATGCATTGCAGGTTCGAAAAAAAGCC
ACCATGGCCATGGCTGGCAATAACGTCATCGTTTGGAACTCTTGTGATTGCTTTACTG
ACTGGTCACATATTTCAAGCTACTGTCCATCGGATTGCTAAAGTTGAAGATGATTTCC
ACAAGATGAGCGAACTCAAGAAGCGTGCAGAAGATGCAGACGTCGCAAAGTCACAG
TTCTTGGCTACTGTTTCACATGAGATCAGAACTCCAATGAATGGTGTTCTAGGGATGC
TCCAAATGCTCATGGATACTGATTTGGACACGACGCAGCAGGACTATGTTAGAACTG
CCCAAGCTAGTGGAAAAGCTTTGGTCTCTCTCATCAATGAGGTTCTTGATCAGGCAA
AGATTGAGTCTGGTAAACTTGAGCTCGAGACGGTGCCCTTTGATCTTAGAACAGTTT
GTGACGACATTTTATCTCTGTTTTGTGGGAAAGCTCAGGAGAAAGGACTGGAGTTAG
CAGTGTATGTCTCGGATCAAGTTCCACAGATACTTATTGGCGATCCTGGCAGGATAA
GACAAATCATTACGAATCTTGTCGGGAACTCCATAAAGTTCACAGAGAGAGGGCATA
TATACCTGACAGTTCATGTAGTTGAAGAGGTCATGAGTTGTTTGGAGGTAGAGACAG
GAATTCAGAACACAAACACTTTAAGTGGCTATCCAGTAGCCAACAGAAGATGTAGCT
GGGAGAGCATTCGGCTTTTCAACAGAGAATTACACTCATCTGAGAAGTCTTTTGCGC
CCATCGCATCTGATTCAATAAGCTTGGTTATATCTGTTGAAGATACTGGCGTCGGCAT
CCCATTTGAAGCCCAATCCCGTGTGTTCACCCCTTTCATGCAGGTAGGTCCATCCATT
GCCCGCATCCATGGGGGCACTGGCATTGGATTAAGCATCAGCAAGTGCTTGGTTGGT
CTCATGAAGGGAGAAATCGGTTTTGCAAGTAAGCCCCATGTTGGTTCTACTTTCACCT
TCACCGCGGTGCTTATGAGGGCACACTGCAAAGGAAATGACATCAAATCATCAGAAT
TTAAAGGGATCAATGCATTGGTTGTTGATCATAGGCCAGTCCGTGCAAAGGTTACCA
AGTATCACTTGCAAAGACTTGGAGTTAAGACCGAACTGACAGCTGAGCTAAATCAGT
TCATTTCTAAATTAAACTCTGGATCACTGACTGCAAAGCTAGTGCTAATAGACAAGG
AAACCTGGCTTAAGGAATCCCATTGCACGCCTCTTCTGGTTAACAAATTGAGGAATA
ATGACAAGCCAGACTCTCCTAAGTTATTTCTTTTGGGGAGCTCTGCAAGTTCTCCCAA
GGGCGGTTCAGATACATCCAGGGAACATAACTTGAATGTAATAATGAAGCCGCTTCG
TGCAAGCATGCTTCAGGTCTCACTACGACGAGCACTAGGTGGGGTCGATAAGGTGCA
CTGCAGGAATGGAGTAGTTGGCAATTCAACATTGGGCAGCCTTCTTCACAAGAAGCA
AATCATTGTTGTCGACGACAATATCGTTAACCTGAAGGTGGCTGGTGCTCTTAAGAA
GTATGGTGCCGAAGTTACTTGTGCAGACAGCGGGAAAAAAGCAATCACATTGCTAA
AACCCCCGCACAATTTTGATGCTTGTTTCATGGACATACAGATGCCAGAAATGGATG
GGTTTGAAGCCACTAGAAGGATTAGAGTGATGGAAAGAGATCTAAATGAGCGAATA
GAACGCGGAGAGGCGCCACCAGAATGTGCTAGTATTCAGAGGTGGCGAACTCCTAT
ATTGGCGATGACGGCGGATGTTATACAGGCAACACACGAGGAGTGCCTGAAAAGCG
AAATGGATGGCTATGTCTCCAAGCCATTTGAAGGGGAGCAGCTGTACAGCGAAGTA
GCGCGGTTTTTCCAAAATCATGACCAAGTTGAATAG
```

Figure 2A (SEQ ID NO:3)

```
MTFARYAVRTAFERPLTSGVAYAVRVTHGEREHFERQQGWTIKKMYSSSNKK
QSSSGPGPGDAAVAEIREPAEEYAPVIFAQDAYKHVISFDMLSGNEDRKNILYS
RKSGKGVLTAPFKLLNNRLGVISTYTVYKSELPANARPHERIQAAIGYLGGIFDIQ
ALVEKLLKQLASQESIMVNVYDTTNENPISMYGDDTGSGMCHVSVLNFGDPSR
KHEMHCRFEKKPPWPWLAITSSFGTLVIALLTGHIFQATVHRIAKVEDDFHKMS
ELKKRAEDADVAKSQFLATVSHEIRTPMNGVLGMLQMLMDTDLDTTQQDYVRT
AQASGKALVSLINEVLDQAKIESGKLELETVPFDLRTVCDDILSLFCGKAQEKGL
ELAVYVSDQVPQILIGDPGRIRQIITNLVGNSIKFTERGHIYLTVHVVEEVMSCLE
VETGIQNTNTLSGYPVANRRCSWESIRLFNRELHSSEKSFAPIASDSISLVISVED
TGVGIPFEAQSRVFTPFMQVGPSIARIHGGTGIGLSISKCLVGLMKGEIGFASKP
HVGSTFTFTAVLMRAHCKGNDIKSSEFKGINALVVDHRPVRAKVTKYHLQRLGV
KTELTAELNQFISKLNSGSLTAKLVLIDKETWLKESHCTPLLVNKLRNNDKPDSP
KLFLLGSSASSPKGGSDTSREHNLNVIMKPLRASMLQVSLRRALGGVDKVHCR
NGVVGNSTLGSLLHKKQIIVVDDNIVNLKVAGALKKYGAEVTCADSGKKAITLLK
PPHNFDACFMDIQMPEMDGFEATRRIRVMERDLNERIERGEAPPECASIQRWR
TPILAMTADVIQATHEECLKSEMDGYVSKPFEGEQLYSEVARFFQNHDQVE
```

Figure 2B

SEQ ID No: 4

HYBRID TYPE HISTIDINE KINASE GENE ISOLATED FROM INDICA RICE IR64

FIELD OF THE INVENTION

The present invention relates to a hybrid-type histidine kinase gene isolated from indica rice IR64, and clones produced thereby.

In particular, the present invention relates to a hybrid-type histidine kinase gene isolated from indica rice IR64 which has been found to be capable of osmosensing and inducible by multiple stresses, and found to be capable of improving the multiple stress tolerance of the crop plants in such a manner that the crop plants thus produced are capable of coping-up with the more than one environmental abiotic stress conditions, and thereby the crop plants have been found to have increased economic value while maintaining the yield thereof.

The present invention also relates to a method of isolation of hybrid-type histidine kinase gene from indica rice IR64, and its sequence listing and its method of cloning, at least, with yeast expression vector and plant expression vector.

The present invention also relates to clones produced by cloning of hybrid-type histidine kinase gene isolated from indica rice IR64 with yeast expression vector and plant expression vector.

The present invention also relates to a method of improving multiple stress tolerance of crop plants by employing hybrid-type histidine kinase gene isolated from indica rice IR64, and crop plants having improved multiple stress tolerance.

The present invention also relates to use of hybrid-type histidine kinase gene isolated from indica rice IR64 improving multiple stress tolerance of crop plants.

The present invention also relates to functional characteristics of hybrid-type histidine kinase gene isolated from indica rice IR64.

BACKGROUND OF THE INVENTION

Rice is an important staple crop for human consumption at the global level. The genome size of rice is about 430 Mb, which is comparatively smaller than various other cereal crops, which varies from about 430 Mb to about 17000 Mb, for example the genome size of the bread wheat is about 16,900 Mb, maize is about 2,600 Mb, sorghum is about 735 Mb, which makes rice the ideal model cereal crop.

It is observed that the environmental stresses are caused either due to biotic factors, for example the virus, bacteria, fungus, insects or nematodes; or due to abiotic factors, for example the extremes of water availability, that is, flooding, and/or extremes of saline condition, that is, higher salinity, and/or extreme shortage of water, that is, drought, and/or extremes of temperature, that is, the temperature being either very high or very low. Collectively these factors affect the potential yield of the crop plants. Further, the changing climatic conditions and global warming have been perceived as potential threats to food self-sufficiency. Owing to the impressive progress made in understanding the plant-pathogen interactions, transgenic plants which are able to survive better under insect attack, which is biotic factor, are now a reality. The common examples of such varieties are Bt cotton and Bt brinjal.

However, the crop plants which can withstand the abiotic stresses are yet to be made available, primarily because abiotic stresses are multigenic in nature.

Therefore, there is an urgent need to modify crop plants so that they become capable of surviving and maintaining a high yield under extreme environmental abiotic stress conditions, and thus, resulting in stress tolerant plants, that is, there is an urgent need to improve multiple stress tolerance of crop plants so that these can overcome problems caused by environmental stresses.

One of the possible ways by which the stress tolerance capability of crops can be enhanced is through genetic engineering where one or more genes are engineered to give the desired trait. With these objectives in mind, several plants have been modified in recent past. One such example involves genes which can synthesize osmolytes to maintain the water potential of the cell under osmotic stress conditions. Other categories include the modification of genes, which are capable of selectively pumping the toxic sodium ions into the vacuole, and thus are capable to keep the cytoplasm free of toxicity.

However, neither much is understood nor much has been made available as far as the sensing machinery associated with the osmotic stresses is concerned.

In lower organisms, for example the yeast, osmosensing is far better understood, and therefore, functional complementation of the yeast osmosensitive mutants with the target gene from crop plants would be a possible way to functionally validate novel genes for similar functions. Genetic modification of crop plants with respect to their osmosensing machinery would be highly desirable since it would result in enhanced tolerance towards osmotic stresses.

Several attempts have been made for the transgenic plants where performance has been enhanced under a specific stress, say salinity or drought or any other abiotic stress. These transgenic plants so far have been utilizing genes which are induced under a single specific stress.

However, no transgenic plant so far has been made available which utilizes the gene which is induced under multiple stresses, and hence, such genes are highly desirable and advantageous, and therefore, the need of the present time is to have a gene which can withstand multiple stresses so that the plant utilizing such gene can withstand multiple stresses while maintaining its potential yield.

Need of the Invention

Therefore, there is an urgent need to have a gene which is capable of osmosensing and is inducible by multiple stresses, and capable of improving the multiple stress tolerance of the crop plants, particularly of the transgenic plants so as to make the plants capable of coping-up with the more than one environmental abiotic stress conditions, and thereby, increasing their economic value while maintaining the yield thereof, and of a method of isolation thereof, and of sequence listing thereof, and of method of cloning of such gene, at least, with yeast expression vector and plant expression vector, and of clones produced thereby on cloning with yeast expression vector and plant expression vector. There is also an urgent need to have a method of improving multiple stress tolerance of crop plants, and crop plants having improved multiple stress tolerance. Further, there is also an urgent need to have functional characteristics of such gene.

Problems to be Solved by the Invention

The present invention, therefore, aims to solve problems of poor stress tolerance of crop plants by providing a gene which should be capable of osmosensing and inducible by multiple stresses, and capable of improving the multiple stress tolerance of crop plants, particularly of transgenic plants so as to make the plants capable of being coping-up with more than one environmental abiotic stress conditions, and method of isolation of such gene from indica rice IR64, and method of improving multiple stress tolerance of crop plants.

Objects of the Invention

Accordingly, the main object of the present invention is to provide a hybrid-type histidine kinase gene which is isolated from indica rice IR64, and is capable of osmosensing and inducible by multiple stresses, and therefore, is capable of improving the multiple stress tolerance of the crop plants so as to make the plants capable of coping-up with the more than one environmental abiotic stress conditions, and hence, increasing the economic value of the crop plants while still maintaining the potential yield thereof.

This is also an object of the present invention to provide a method of isolation of hybrid-type histidine kinase gene which is isolated from indica rice IR64.

This is also an object of the present invention to provide a sequence listing of the hybrid-type histidine kinase gene which is isolated from indica rice IR64.

This is also an object of the present invention to provide method of cloning the hybrid-type histidine kinase gene which is isolated from indica rice IR64, at least, with yeast expression vector and the plant expression vector.

This is also an object of the present invention to provide clones produced by cloning of hybrid-type histidine kinase gene isolated from indica rice IR64 with yeast expression vector and the plant expression vector.

This is also an object of the present invention to provide functional characteristics of the hybrid-type histidine kinase gene which is isolated from indica rice IR64.

This is also an object of the present invention to provide a method for improving multiple stress tolerance of crop plants by employing hybrid-type histidine kinase gene isolated from indica rice IR64.

This is also an object of the present invention to provide crop plants having improved multiple stress tolerance.

This is also an object of the present invention to provide use of hybrid-type histidine kinase gene isolated from indica rice IR64 to improve multiple stress tolerance of crop plants.

The other objects and advantages will be more apparent from the following description and nature of the invention when it is read in conjunction with the accompanying figures, which are not intended to limit its scope.

BRIEF DESCRIPTION OF THE ACCOMPANYING FIGURES OF THE INVENTION

FIG. 2A illustrates the complete Gene sequence of open reading frame [ORF] of OsHk3b in accordance with the most preferred embodiment of the present invention (SEQ ID No: 3).

FIG. 2B illustrates the complete deduced amino acid sequence for protein encoded by ORF of OsHk3b in accordance with the most preferred embodiment of the present invention (SEQ ID No: 4).

Figure 6:
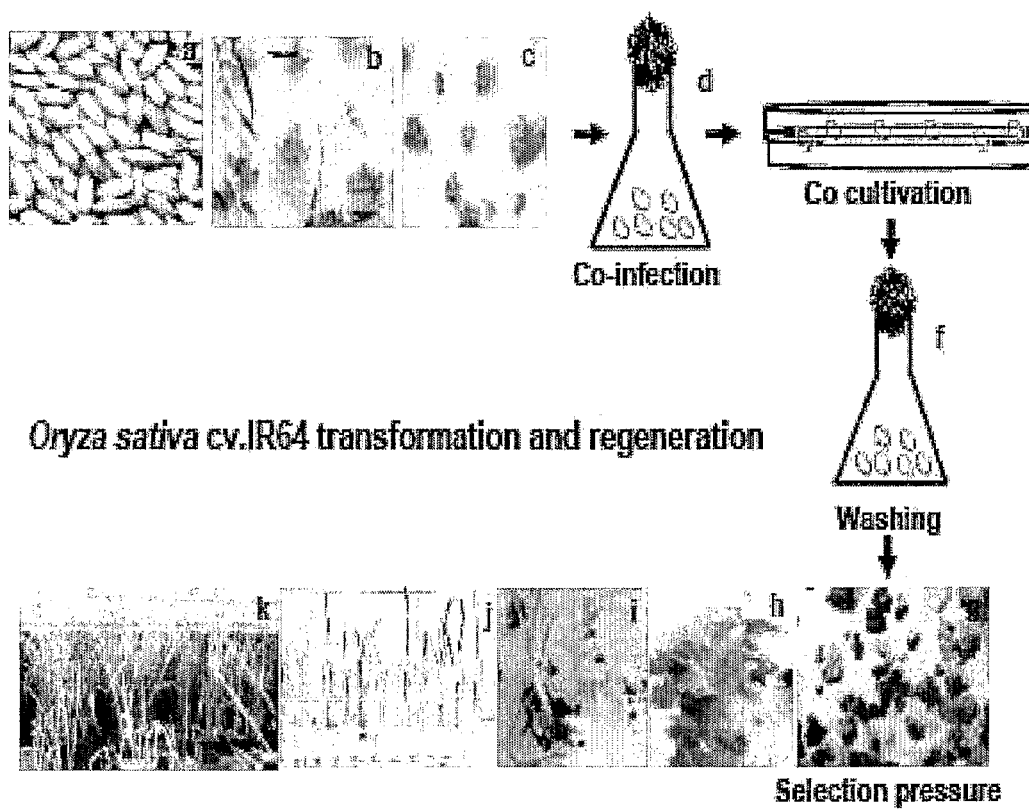

FIG. 6 *Oryza sativa* cv IR64 transformation and regeneration—illustrates seeds of rice IR-64 step—[a]; rice callus formation on callus induction media step—[b]; sub-cultured rice callus kept on callus induction media for about 5-7 days step —[c]; co-infection of rice calli with *Agrobacterium* strain LBA4404 containing OsHK3b construct step—[d]; co-cultivation of co-infected rice calli step—[e]; washing of overgrown *Agrobacterium* with antibiotic cefotaxim step—[f]; transfer of washed callus on selection plate step—[g]; transformed callus kept on regeneration medium step—[h]; regenerated plantlets as transferred on fresh regeneration medium step—[i]; completely regenerated plant as transferred into culture tubes for hardening step—[j]; transgenic plant from step—[j] is further transferred into Earthen pot and kept in green house step—[k] in accordance with the most preferred embodiment of the present invention.

Figure 7A:
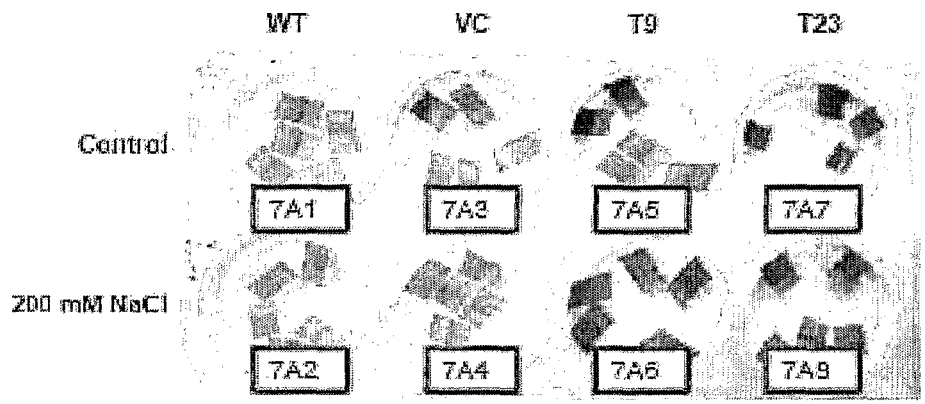

FIG. 7A is illustrative of confirmation of multiple stress tolerance of leaves of plant grown in FIG. 6 by leaf disc assay showing the bleaching rate of different leaf samples under control and salinity stress conditions in accordance with the most preferred embodiment of the present invention.

Figure 7B:
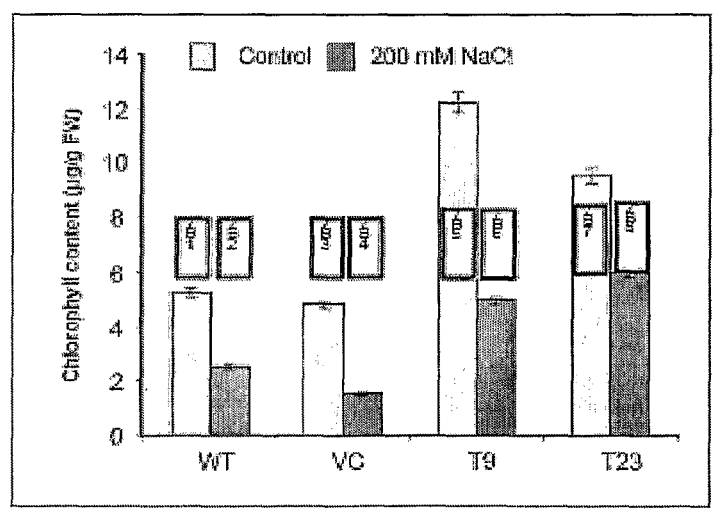

FIG. 7B illustrates total chlorophyll content of the leaves of plant grown in FIG. 6 in accordance with the most preferred embodiment of the present invention.

Figure 8:
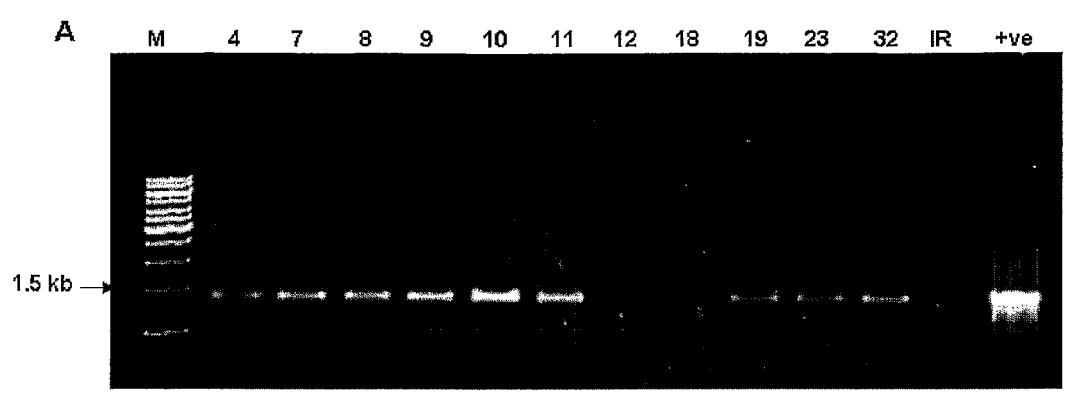

FIG. 8 is illustrative of confirmation of successful integration of OsHK3b gene of present invention into genome of IR64 transgenic plants using plasmid—pCAMBIA1304 in accordance with most preferred embodiment of the present invention.

Figure 9:
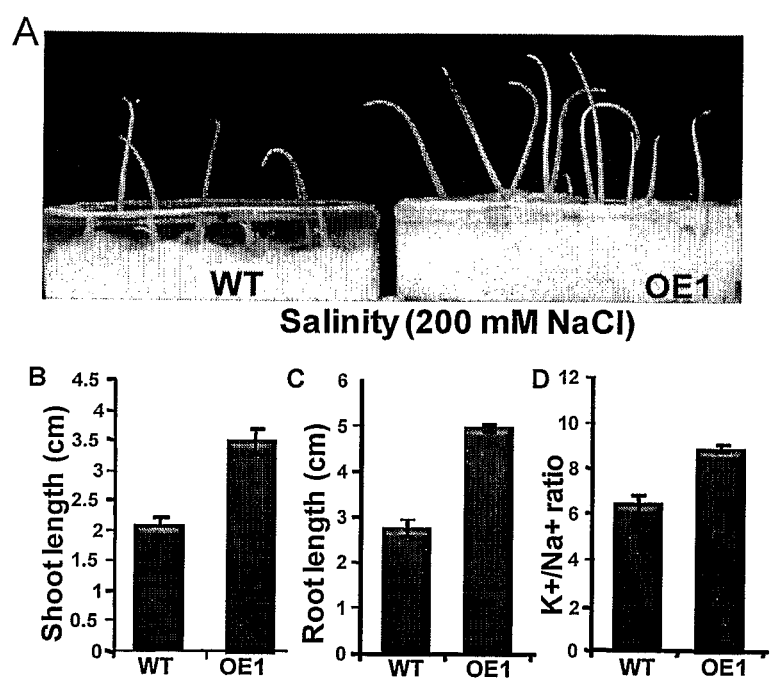

FIG. 9 is illustrative of confirmation of multiple stress tolerance of $T_1$ plants, in terms of seed germination under saline conditions, grown from seeds of plants grown in FIG. 6 in accordance with the most preferred embodiment of the present invention.

Figure 10:
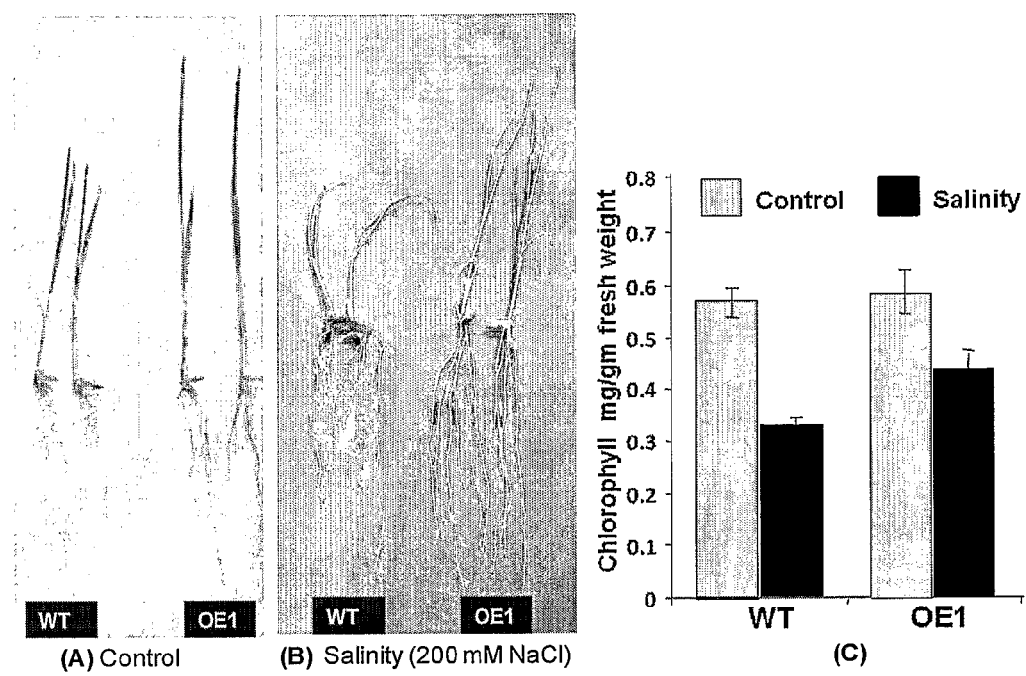

FIG. 10 is illustrative of comparative confirmation of multiple stress tolerance of $T_1$ plants grown for 7 days under normal conditions, and thereafter, grown for another 10 days under saline conditions by measuring its chlorophyll contents.

The detailed legends of the Figures have been provided at the end of this description.

DESCRIPTION AND PREFERRED EMBODIMENTS OF THE INVENTION

It is now understood that prior art neither discloses nor teaches that hybrid-type histidine kinase gene having capability of osmosensing and inducible by multiple stresses, and capability of improving the multiple stress tolerance of crop plants, particularly of transgenic plants can be isolated from indica rice IR64.

Further, the prior art neither discloses nor teaches that hybrid-type histidine kinase gene isolated from indica rice IR64 can be cloned, at least, with yeast expression vector and the plant expression vector.

Further, the prior art neither discloses nor teaches that crop plants can be improved for their multiple stress tolerance by employing such isolated gene so as to make the plants capable of being coping-up with more than one environmental abiotic stress conditions to solve problems of poor stress tolerance of crop plants.

With aim to isolate a hybrid-type histidine kinase gene from indica rice IR64, the inventors have surprisingly found that if cDNA isolated from IR64 seedling is treated by polymerase chain reaction (PCR) with forward primer OsHk3bF and reverse primer OsHk3bR, wherein step of annealing is carried out at about 55° C., then hybrid-type histidine kinase gene gets isolated, and the isolated gene has been surprisingly found to have capability of osmosensing and inducible by multiple stresses, and capability of improving the multiple stress tolerance of crop plants, particularly of transgenic plants.

With aim to clone hybrid-type histidine kinase gene isolated from indica rice IR64, at least, with yeast expression vector and the plant expression vector, the inventors have surprisingly found that isolated gene upon amplifying by treatment with forward primer OsHk3bSpeIF and reverse primer OsHk3bSpeIR by employing polymerase chain reaction (PCR), the gene of present invention gets cloned into yeast expression vector and also into plant expression vector.

With aim to improve multiple stress tolerance of crop plants, the inventors have surprisingly found that when calli grown from seeds of IR64 are co-infected with a medium containing cloned gene, the IR64 gets transformed and grows to a complete transgenic IR64 plant having overexpression of gene of present invention, and such grown transgenic plants have been surprisingly found to have improved multiple stress tolerance against more than one environmental stresses, meaning thereby such grown plants have been found to be capable of surviving better under the abiotic stress conditions.

It has also been found that seeds of transgenic plants grown by employing clones of gene of present invention also have improved multiple stress tolerance during seed germination, and both, root and shoot, surprisingly, do not demonstrate reduced growth, and the plants grown therefrom have also been found to have improved multiple stress tolerance as compared to germination of seeds of normal crop plants and plants grown therefrom. Therefore, the problems of poor stress tolerance of crop plants have been solved by present invention.

Accordingly, the present invention relates to method for isolation of hybrid-type histidine kinase gene from the indica rice IR64, comprising treatment of cDNA isolated from IR64 seedling with forward primer OsHk3bF and reverse primer OsHk3bR by polymerase chain reaction (PCR), wherein step of annealing is carried out at about 55° C., and wherein hybrid-type histidine kinase gene—OsHK3b is isolated from its plasmid pTOPO-OSHK3b.

Figures 1A, 1B, 1C:
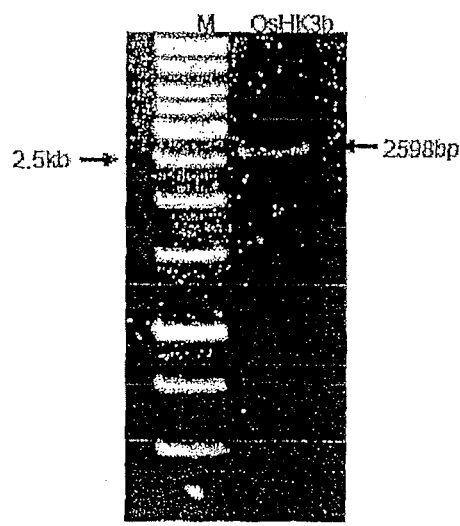
FIG. 1A illustrates primer sequences (SEQ ID No: 1 and (SEQ ID No: 2) used for the isolation of gene from indica rice IR64 in accordance with the most preferred embodiment of the present invention.
FIG. 1B illustrates various conditions for polymerase chain reaction (PCR) for the isolation of the gene from indica rice IR64 and cloning thereof in accordance with the most preferred embodiment of the present invention.
FIG. 1C illustrates agarose gel electrophoresis of polymerase chain reaction (PCR) product showing an amplification product of a size of about 2.6 Kb, more precisely of size of about 2598 bp of the gene isolated from indica rice IR64 in accordance with the most preferred embodiment of the present invention.

In accordance with present invention, the forward primer OsHk3bF is identified as 5'ATGACGTTCGCGAGG-TACGC3' (SEQ ID NO: 1) and reverse primer OsHk3bR is identified as 5'CTATTCAACTTGGTCATGATTTTG3' (SEQ ID NO: 2) (FIG. 1A).

In accordance with present invention, the primers were synthesized by:— a) aligning amino acids sequence (protein) of the SLN1 (osmosensor) of yeast with amino acid sequences (Protein) of 14 members of histidine kinase [HK] family in rice (*Oryza sativa japonica*), wherein one member of HK family—OsHk3b in rice (*Oryza sativa japonica*) among the 14 members family was found to be more close to SLN1 (osmosensor) of yeast;

b) based on amino acid sequences of OsHk3b from rice (*Oryza sativa japonica*), its corresponding nucleotide sequence is taken;

c) analyzing its ORF using commercially available software;

d) designing forward primer OsHk3bF identified as 5'ATGACGTTCGCGAGGTACGC3' (SEQ ID NO: 1) and reverse primer OsHk3bR identified as 5' CTATTCAACT-TGGTCATGATTTTG3' (SEQ ID NO: 2) from ORF of OsHk3b using commercially available primer designing software;

e) identifying nucleotide sequences of forward primer and reverse primer; and f) preparing forward primer OsHk3bF identified as 5'ATGACGTTCGCGAGGTACGC3' (SEQ ID NO: 1) and reverse primer OsHk3bR identified as 5' CTATTCAACT-TGGTCATGATTTTG3' (SEQ ID NO: 2).

In accordance with one of the preferred embodiments of the present invention, analysis of ORF may be performed by conventionally known means.

In accordance with one of the preferred embodiments of the present invention, designing of forward primer OsHk3bF identified as 5'ATGACGTTCGCGAGGTACGC3' (SEQ ID NO: 1) and reverse primer OsHk3bR identified as 5'CTAT-TCAACTTGGTCATGATTTTG3' (SEQ ID NO: 2) from ORF of OsHk3b may be carried out by conventionally known means.

In accordance with present invention, cDNA is isolated from seedlings of rice IR64, particularly from seedlings of rice cv IR64 comprising following steps:— a) isolating total RNA from salinity stressed leaf tissue of IR64 seedling;

b) isolating mRNA from total RNA by employing the streptavidin paramagnetic beads and biotin-labeled oligo $d(T)_{20}$ primer;

c) synthesizing first strand cDNA from mRNA by employing conventionally available first strand cDNA synthesis kit.

In accordance with present invention, the polymerase chain reaction (PCR) comprises steps of:— i) preparing reaction mixture of cDNA, and forward primer OsHk3bF identified as 5'ATGACGTTCGCGAGG-TACGC3' (SEQ ID NO: 1) and reverse primer OsHk3bR identified as 5'CTATTCAACTTGGTCATGATTTTG3' (SEQ ID NO: 2);

ii) initial denaturation of reaction mixture from step—i) at about 94° C. preferably for about 5 min;

iii) denaturation of reaction mixture from step—ii) for about 34 cycles at about 94° C. preferably for about 1 min;

iv) annealing of reaction mixture from step—iii) at about 55° C. preferably for about 1 min;

v) extension of reaction mixture from step—iv) at about 72° C. preferably for about 3 min; and vi) final extension of reaction mixture from step—v) at about 72° C. preferably for about 7 min.

In accordance with present invention, the method for isolation of hybrid-type histidine kinase gene from the indica rice IR64, further comprises following steps:—
1) preparing pTOPO-OsHK3b recombinant plasmid by cloning amplified fragment of gene into TOPO-TA2.1 vector;
2) isolating the gene—OsHK3b from pTOPO-OsHK3b recombinant plasmid using standard M13 forward and reverse primers;
wherein isolation of gene—OsHK3b is confirmed [identified] by size of DNA which is about 2.6 Kb, more precisely about 2598 bp.

In accordance with present invention, after performing polymerase chain reaction [PCR] with selected primer many copies of target DNA are made, which is not seen in solution but when ligated into TOPO-TA cloning vector which stabilizes target DNA, the transformed colonies can be seen, however the amplified product can be visualized upon electrophoresis in agarose coupled to staining with ethidium bromide. The TOPO-TA is only used for stabilization of amplified product that also make easy for sequencing. The gene formed means putative isolation. After formation as in FIG. 1C isolation is confirmed by sequencing, band on the agarose gel confirms that it has been isolated.

In one embodiment, the present invention relates to hybrid-type histidine kinase gene isolated from indica rice IR64, and the isolated gene has been found to be capable of acting as osmosensor, and having capability of osmosensing and inducible by multiple stresses, and capability of improving the multiple stress tolerance of crop plants, particularly of transgenic plants so as to make the plants capable of coping-up with more than one environmental abiotic stress conditions, and hence, to increase their economic value while maintaining its potential yield.

In another embodiment, the present invention relates to sequence listing of the hybrid-type histidine kinase gene isolated from indica rice IR64, wherein the gene is sequenced after formation of the pTOPO-OsHK3b recombinant plasmid, and wherein complete Gene sequence of open reading frame [ORF] of gene—OsHk3b is 2598 bp and is as given in accompanying FIG. 2A a reference to which is drawn here, and wherein the gene—OsHK3b of present invention has been submitted to National Center for Biological Resources (NCBI) under GenBank accession number Bankit 1121378 FJ004641 on Aug. 7, 2008. The copy of acknowledgment from the National Center for Biological Resources (NCBI) is enclosed.

In one embodiment, the present invention relates to a hybrid-type histidine kinase gene, the complete Gene sequence of open reading frame [ORF] thereof—OsHk3b is 2598 bp and as given in FIG. 2A.

In accordance with one embodiment of present invention, hybrid-type histidine kinase gene—OsHK3b is identifiable by GenBank accession number Bankit 1121378 FJ004641 of National Center for Biological Resources (NCBI).

In another embodiment, the present invention relates to a method of cloning the hybrid-type histidine kinase gene isolated from indica rice IR64 into yeast expression vector namely—pYES2, comprising steps of:—
a) amplifying gene—OsHk3b from pTOPO-OsHK3b plasmid by treating pTOPO-OsHK3b plasmid with forward primer OsHk3bSpeIF and reverse primer OsHk3bSpeIR by employing polymerase chain reaction [PCR];
wherein the amplified fragment of OsHk3b gene containing the complete open reading frame [ORF] of the gene along with additional SpeI site—OsHk3b gets cloned into XbaI site of pYES2.

In accordance with present invention, the primers employed for cloning the isolated gene are same as employed to isolate the gene, but the primers for cloning the isolated gene contains additional SpeI site that facilitates cloning of OsHk3b gene into pYES2.

In accordance with preferred embodiment of the present invention, after polymerase chain reaction [PCR] of OsHk3b with forward primer OsHk3bSpeIF and reverse primer OsHk3bSpeIR, pYES2 is added.

In accordance with present invention, the polymerase chain reaction [PCR] to amplify the gene—OsHk3b from pTOPO-OsHK3b plasmid comprises steps of:—
i) preparing reaction mixture of pTOPO-OsHK3b plasmid, and forward primer OsHk3bSpeIF and reverse primer OsHk3bSpeIR;
ii) initial denaturation of reaction mixture from step—i) at about 94° C. preferably for about 5 min;
iii) denaturation of reaction mixture from step—ii) for about 34 cycles at about 94° C. preferably for about 1 min;
iv) annealing of reaction mixture from step—iii) at about 55° C. preferably for about 1 min;
v) extension of reaction mixture from step—iv) at about 72° C. preferably for about 3 min; and
vi) final extension of reaction mixture from step—v) at about 72° C. preferably for about 7 min In accordance with preferred embodiment of the present invention, after polymerase chain reaction [PCR] of OsHk3b with forward primer OsHk3bSpeIF and reverse primer OsHk3bSpeIR, pYES2 is added.

In another embodiment, the present invention relates to a clone of hybrid-type histidine kinase gene isolated from indica rice IR64 into yeast expression vector namely—pYES2, which is identified as pYES2-OsHk3b.

In another embodiment, the present invention relates to a method of cloning the hybrid-type histidine kinase gene isolated from indica rice IR64 into plant expression vector, preferably rice expression vector namely—pCAMBIA1304, comprising steps of:—
a) amplifying gene—OsHk3b from pTOPO-OsHK3b plasmid by treating pTOPO-OsHK3b plasmid with forward primer OsHk3bSpeIF and reverse primer OsHk3bSpeIR by employing polymerase chain reaction [PCR];
wherein the amplified fragment of OsHk3b gene containing the complete open reading frame [ORF] of the gene along with additional SpeI site—OsHk3b gets cloned into SpeI site of pCAMBIA1304.

In accordance with present invention, the primers employed for cloning the isolated gene are same as employed to isolate the gene, but the primers for cloning the isolated gene contains additional SpeI site that facilitates cloning of OsHk3b gene into pCAMBIA1304.

In accordance with preferred embodiment of the present invention, after polymerase chain reaction [PCR] of OsHk3b with forward primer OsHk3bSpeIF and reverse primer OsHk3bSpeIR, pCAMBIA1304 is added.

In accordance with present invention, the polymerase chain reaction [PCR] to amplify the gene—OsHk3b from pTOPO-OsHK3b plasmid comprises steps of:—
i) preparing reaction mixture of pTOPO-OsHK3b plasmid, and forward primer OsHk3bSpeIF and reverse primer OsHk3bSpeIR;

ii) initial denaturation of reaction mixture from step—i) at about 94° C. preferably for about 5 min;

iii) denaturation of reaction mixture from step—ii) for about 34 cycles at about 94° C. preferably for about 1 min;

iv) annealing of reaction mixture from step—iii) at about 55° C. preferably for about 1 min;

v) extension of reaction mixture from step—iv) at about 72° C. preferably for about 3 min; and vi) final extension of reaction mixture from step—v) at about 72° C. preferably for about 7 min In accordance with preferred embodiment of the present invention, after polymerase chain reaction [PCR] of OsHk3b with forward primer OsHk3bSpeIF and reverse primer OsHk3bSpeIR, pCAMBIA1304 is added.

In another embodiment, the present invention relates to a clone of hybrid-type histidine kinase gene isolated from indica rice IR64 into rice expression vector namely—pCAMBIA1304, which is identified as pCAMBIA1304-OsHk3b.

In one embodiment, the present invention relates to a method for improving multiple stress tolerance of crop plants, comprising co-infecting rice calli grown from seeds of IR64 with a medium containing cloned gene and allowing the co-infected calli into complete transgenic IR64 plant, wherein the medium is *Agrobacterium* strain LBA4404, and cloned gene is pCAMBIA1304-OsHk3b.

In accordance with present invention, a method for improving multiple stress tolerance of crop plants, comprises steps of:— a) co-infecting rice calli grown from seeds of IR64 with a medium containing cloned gene;
b) co-cultivating the co-infected rice calli from step—a);
c) washing overgrown medium from co-cultivated rice calli from step—b) with antibiotic;
d) transferring the washed callus from step—c) on a selection plate for growth of transformed calli;
e) treating the transformed calli from step—d) with regeneration media;
f) repeating step of treatment of transformed calli from step—e) with fresh regeneration media till it forms a completely regenerated plant;
g) hardening the completely regenerated plant from step—f) in a culture tube;
h) transferring the hardened plant from step—g) to earthen pot for development into a complete transgenic IR64 plant;

wherein the medium is *Agrobacterium* strain LBA4404, and cloned gene is pCAMBIA1304-OsHk3b.

In accordance with one of the preferred embodiments of the present invention, step—b) of co-cultivation performed by keeping the co-infected rice calli from step a) in dark for about 48 hours.

In accordance with one of the preferred embodiments of the present invention, the culture tube in step—g) contains regenerating rice plants in regenerating media.

In accordance with present invention, the antibiotic is cefotaxim, and the regeneration media comprises commercially available Moorashige and Skoog media (Sigma, India).

In one embodiment, the present invention relates to crop plants having improved multiple stress tolerance, as produced by employing clone of gene isolated from indica rice IR64 of present invention, wherein the transgenic plants have been found to have overexpression of hybrid-type histidine kinase gene isolated from indica rice IR64, and improved multiple stress tolerance against more than one environmental stresses, meaning thereby transgenic plants produced in accordance with present invention have been found to be capable of surviving better under the abiotic stress conditions, and therefore, overcoming problems of poor stress tolerance.

In one embodiment, the present invention relates to second generation plants produced from seeds of first generation transgenic plants which were grown by employing clones of gene of present invention, wherein subsequently [second generation] grown transgenic plants have also been found to have improved multiple stress tolerance, and even during seed germination of first generation of transgenic plants, root and shoot, surprisingly, were found to demonstrate better growth, at least, were not found to demonstrating reduced growth. On the contrary, when a plant is grown from seedlings which were not infected with clones of gene of present invention were found to have poor tolerance to environmental stresses, and during further germination of seeds from these normal [control] plants, growth of root and shoot were found to be slow.

In one embodiment, the present invention relates to use of hybrid-type histidine kinase gene isolated from indica rice IR64, to improve multiple stress tolerance of crop plants.

The present invention is now described with reference to accompanying figures.

In accordance with the most preferred embodiment of the present invention, it comprises following steps:—

A] Isolation of a Hybrid-Type Histidine Kinase Gene from Indica Rice IR64:—

In accordance with the most preferred embodiment of the present invention, the full length gene, that is, a stretch of DNA coding for a protein, of OsHK3b is isolated from rice cv IR64 essentially employing the polymerase chain reaction (PCR) which is carried out by essentially by employing the forward primer OsHk3bF identified as 5'ATGACGTTCGCGAGGTACGC3' (SEQ ID NO: 1) and reverse primer OsHk3bR identified as 5'CTATTCAACTTGGTCATGATTTTG3' (SEQ ID NO: 2) (FIG. 1A), which have been judicially selected. It has been surprisingly observed that if an attempt is made to isolate the desired gene from rice IR 64 by employing any other primer, the desired gene does not isolate.

In accordance with this invention, the polymerase chain reaction (PCR) is carried out under the conditions as illustrated in the FIG. 1B which have also been judicially selected. It has been surprisingly observed that if an attempt is made to carry out the PCR reaction at the conditions different than the conditions illustrated in accompanying FIG. 1B, the desired gene does not isolate.

In accordance with this invention, the PCR conditions [FIG. 1B] are—initial denaturation is carried out at about 94° C. for about 5 min followed by about 34 cycles of denaturation carried out at about 94° C. for about 1 min, annealing at about 55° C. for about 1 min, extension at about 72° C. for about 3 min and final extension at about 72° C. for about 7 min by employing the OsHk3bF and OsHk3bR primers [FIG. 1B].

In accordance with the present invention, the total RNA is isolated from salinity stressed leaf tissue of IR64 seedling. Followed by isolation of the mRNA from total RNA by employing the streptavidin paramagnetic beads and biotin-labeled oligo d(T)$_{20}$ primer. The first strand cDNA is synthesized from mRNA by employing the first strand cDNA synthesis kit. The polymerase chain reaction [PCR] is carried out as described herein above. The amplified fragment is cloned into TOPO-TA2.1 vector to get pTOPO-OsHK3b recombinant plasmid. The accompanying FIG. 1C illustrates a PCR amplified product from the plasmid pTOPO-OsHK3b using standard M13 forward and reverse primers. The size of this DNA as seen from the gel (FIG. 1C) is about 2.6 Kb, more precisely about 2598 bp of OsHk3b, which confirms that the gene—OsHK3b has been isolated.

B] Sequencing of a Hybrid-Type Histidine Kinase Gene Isolated from Indica Rice IR64:—

In accordance with the present invention, in one embodiment, the gene isolated from indica rice IR 64 is sequenced after formation of the pTOPO-OsHK3b recombinant plasmid. The DNA sequence as obtained after sequencing is illustrated in the accompanying FIG. 2A, which illustrates the complete Gene sequence of ORF of OsHk3b which is 2598 bp and has been submitted to National Center for Biological Resources (NCBI) under GenBank accession number Bankit 1121378 FJ004641 on Aug. 7, 2008. The copy of acknowledgment from the National Center for Biological Resources (NCBI) is enclosed.

In accordance with this invention, the DNA sequence as obtained is analyzed using BLAST search, which surprisingly has been found to be homologous to the known gene classified as the hybrid type histidine kinase gene of other organisms with minor variations belonging only to the rice IR64. Further, the isolated cDNA has been confirmed to have about 2598 bp length of ORF which is capable of encoding a polypeptide of about 865 amino acid residues (FIG. 2B). The predicted molecular mass of deduced polypeptide is found to be about 95.90 kDa. The predicted protein contains both—a transmitter and—a receiver domain. These are characteristic features of a hybrid type histidine kinase. It also showed a conserved histidine residue at 291 position as illustrated in the accompanying FIG. 2B by underlining in line 6 from top in the transmitter domain and a conserved aspartate residue at 772 position as illustrated in the accompanying FIG. 2B by underlining in second line from bottom in the receiver domain. The accompanied FIG. 2B illustrates the complete deduced amino acid sequence for protein encoded by ORF of OsHk3b which is about 95.9 kDa, wherein the transmitter domain has a conserved Histidine residue at 291 position (H, underlined therein). The receiver domain has a conserved Aspartate residue at position 771 (D, underlined therein).

Accordingly, the present invention provides a gene from indica rice cv IR64 which possess all characteristic feature of the hybrid type histidine kinase gene. The DNA sequence of the isolated OsHk3b gene has also been submitted to National Center for Biological Resources (NCBI) under the accession number bankit1121378 on Aug. 7, 2008. The copy of acknowledgment from the National Center for Biological Resources (NCBI) is enclosed.

C] Cloning of a Hybrid-Type Histidine Kinase Gene Isolated from Indica Rice Ir64:—

C1] Cloning into Yeast Expression Vector—pYES2:—

Figure 3A:
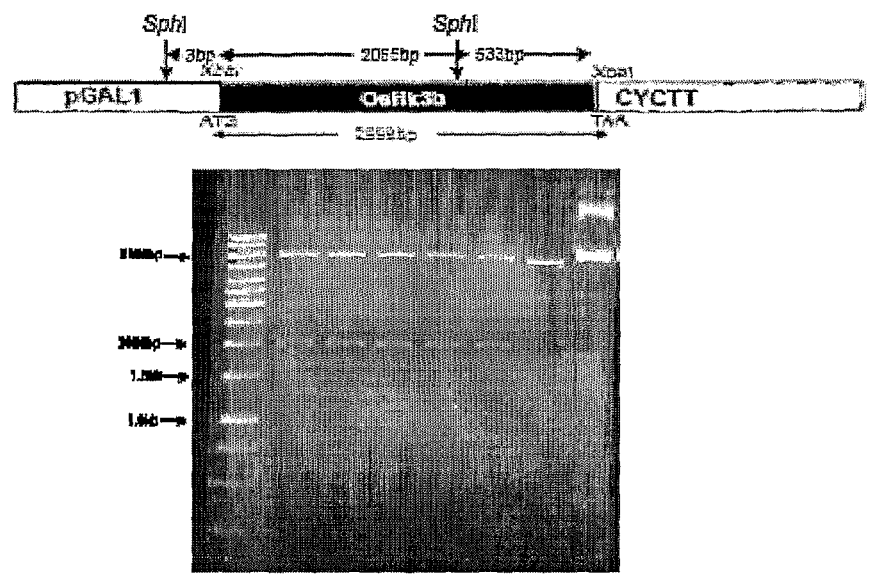
FIG. 3A illustrates confirmation of cloning of gene of the present invention into the pYES2 vector in accordance with the most preferred embodiment of the present invention.

In accordance with present invention, the gene—OsHk3b of the present invention is cloned into yeast expression vector namely—pYES2 by amplifying the gene—OsHk3b from pTOPO-OsHK3b by employing OsHk3bSpeIF and OsHk3bSpeIR primers as illustrated in the accompanying FIG. 1A by employing the polymerase chain reaction [PCR] under the conditions as illustrated in the accompanying FIG. 1B, wherein the amplified fragment containing the complete open reading frame [ORF] of the gene—OsHk3b is cloned into XbaI site of pYES2 and in-frame cloning is confirmed by restriction digestion using SphI [FIG. 3A], wherein the restriction digestion of pYES2-OsHk3b plasmid with SphI to confirm the orientation of OsHK3b ORF; M: 1 kb DNA ladder; 1,2,3,4 and 5 are pYES2-OsHK3b plasmid; 6: pYES2 and 7: undigested pYES2–OsHk3b plasmid, and the schematic representation of pYES2-OsHk3b has been shown on the top of figure.

Accordingly, the present invention provides a gene—OsHk3b which is capable of being cloned into yeast expression vector pYES2-OsHk3b and produces the clone of gene—OsHk3b into yeast expression vector pYES2-OsHk3b.

C2. Cloning into Plant Expression Vector—pCAMBIA1304

Figure 3B:
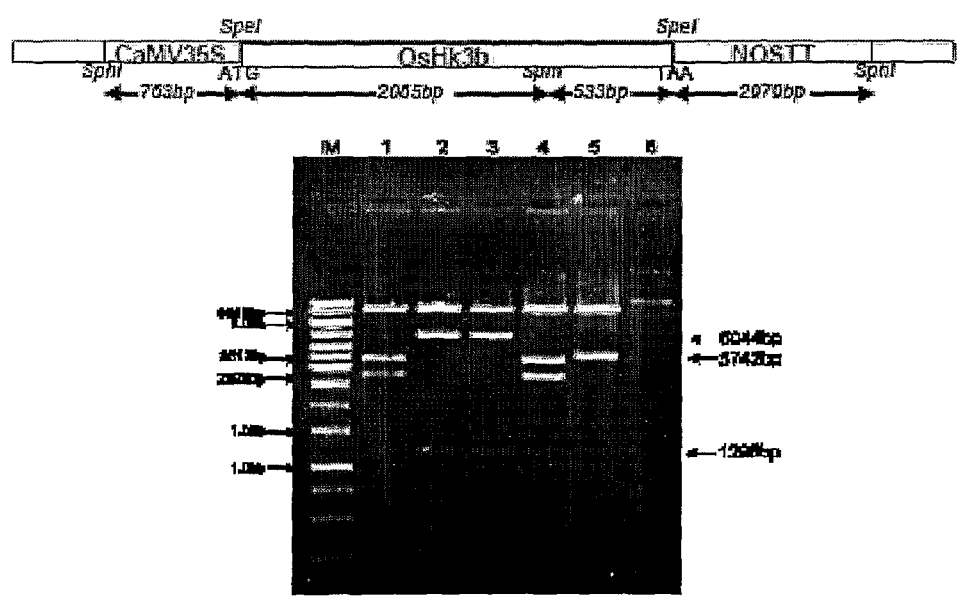
FIG. 3B illustrates confirmation of cloning of gene of the present invention into the pCAMBIA1304 vector in accordance with the most preferred embodiment of the present invention.

In accordance with present invention, the gene—OsHk3b of the present invention is cloned into plant expression vector namely—pCAMBIA1304 by amplifying the gene—OsHk3b from pTOPO-OsHK3b by employing OsHk3bSpeIF and OsHk3bSpeIR primers as illustrated in the accompanying FIG. 1A by employing the polymerase chain reaction [PCR] under the conditions as illustrated in the accompanying FIG. 1B, wherein the amplified fragment containing the complete open reading frame of the gene—OsHk3b is cloned into SpeI site of pCAMBIA1304 and in-frame cloning is confirmed by restriction digestion using SphI [FIG. 3B], wherein restriction digestion of pCAMBIA1304-OsHK3b plasmid with SphI to confirm the orientation of OsHk3b ORF; M: 1 kb DNA ladder; 1,2,3 and 4: pCAMBIA1304-OsHK3b plasmid; 5: pCAMBIA1304 and 6: undigested pCAMBIA1304-OsHK3b plasmid. Schematic representation of pCAMBIA1304-OsHk3b has been shown on the top of figure.

Accordingly, the present invention provides a gene—OsHk3b which is capable of being cloned into plant expression vector pCAMBIA1304-OsHk3b and produces the clone of gene—OsHk3b into plant expression vector pCAMBIA1304-OsHk3b.

D] Functional Characterization [Advantages] of a Hybrid-Type Histidine Kinase Gene Isolated from Rice IR 64:—

D1] To establish that the presently provided gene—OsHk3b is capable of functioning as an osmosensor, i.e. its advantage in rescuing the osmosensitive mutation in yeast, the Yeast (*Saccharomyces cerevisiae*) strain HS13 with a temperature-sensitive mutation in SLN1 gene is employed for complementation experiments (sln-Ts) in accordance with the preferred embodiment of the present invention. It is observed that the HS13 mutant grow well at 28° C. (FIG. 4A) but fail to grow at 37° C. (FIG. 4B) on YPD media (Yeast, Peptone and Dextrose media) as well as on YPD containing salt (200 mM NaCl). In accordance with the present invention, the HS13 mutant is transformed with (i) pYES2-OsHk3b, (ii) vector pYES2 (vector without OsHk3b) and (iii) functional sln1 gene (from yeast) to produce a modified HS 13 strain which is tested further. Further, in accordance with the present invention, the HS13 carrying pYES2 (vector without OsHk3b) works as negative control (VC) while HS13 carrying functional sln1 gene works as positive control (SLN1). When all these strains are streaked on YPD media and incubated either at 28° C. or at 37° C., it is surprisingly observed that after about 72 h of incubation, HS13 transformed with pYES2-OsHk3b and HS13 carrying functional sln1 gene are able to grow even at 37° C. (FIG. 4B), whereas HS13 alone or HS13 carrying pYES2 (VC) are not able to grow at 37° C., thereby confirms that the complementation of sln1 mutant with OsHk3b is achievable, indicating the advantage of gene—OsHk3b in rescuing the osmosensitive mutation in yeast.

After having established the advantage of the gene—OsHk3b as osmosensor which may be used to improve tolerance towards salinity stress, an attempt is made to find out the mode of action of this gene by checking the role of conserved Histidine and/or Aspartate residue of OsHk3b gene, site directed mutagenesis of OsHk3b gene are carried out to mutate the conserved Histidine residue of transmitter domain into Valine (HK3H*, HS13 carrying histidine mutated OSHK3H291V) and conserved Aspartate residue into Glutamate (HK3D*, HS13 carrying aspartate mutated OSHK3D772E) in the expressed OsHk3b protein. [Site directed mutagenesis of pYES2-OsHk3b is carried out to mutate the conserved Histidine residue of transmitter domain into Valine using forward primer, OSHK3bHisMUTF GGC-TACTGTTTCAGTTGAGATCAGAACTC (SEQ ID NO: 5) and reverse primer, OSHK3bHisMUTR AGTTCTGATCT-CAACTGAAACAGTAGCC (SEQ ID NO: 6); whereas conserved Aspartate residue into Glutamate using forward primer, OSHK3bAspMUTF GATGCTTGTTTCATGCT-CATACAGATGCCAG (SEQ ID NO: 7) and reverse primer, OSHK3bAspMUTR-CTGGCATCTGTATGAGCAT-GAAACAAGCATC (SEQ ID NO: 8) using quick change site directed mutagenesis kit].

The above analysis confirms that the mutation in the yeast HS13, transformed with these mutated OsHk3b conserved residues could not complement the sln1-Ts mutant allele containing host HS13 at 37° C. (FIG. 4B), which confirms that OsHk3b is a confirmed hybrid type Histidine kinase and conserved Histidine and Aspartate are involved in the phosphorylation process for the growth of HS13 at 37° C. Further, the transformed yeast (OsHk3b) is found to be capable to tolerate the salinity stress upto 200 mM NaCl (YPD containing 200 mM NaCl), whereas the vector transformed (VC) or the untransformed HS13 cells could not survive at 37° C. (FIG. 4D). This analysis clearly establishes that the protein encoding OsHk3b gene is capable of acting as an osmosensor and can be used for improving of tolerance towards salinity stress.

D2] To establish that the presently provided gene—OsHk3b is inducible by different abiotic stresses, a real time PCR analysis (qRT-PCR) is performed to quantify the expression of its mRNA. This analysis is carried out using various cDNA samples made from the mRNA of IR64 seedlings which are subjected to various abiotic stresses, i.e., salinity (S), drought (D), ABA (Abscisic acid), Heat (42° C.) and Cold (4° C.) for about 8 hours and about 24 hours. The real time PCR amplification results as illustrated in the histogram in FIG. 5, surprisingly indicate the inducibility of this gene by the different environmental signal in the form of abiotic stresses. Further, differential regulation of OsHk3b transcripts under salinity, drought, ABA, Heat and cold could also be seen surprisingly. The accumulation of OsHK3b transcript increases with time from about 8 hours to about 24 hours in all the stress conditions such as under salinity (FIG. 5B, C), drought (FIG. 5D, E), ABA (FIG. 5F, G), heat (FIG. 5H, I) and cold (FIG. 5J, K), thereby indicating the role of this gene in multiple abiotic stresses, and hence, its advantage in improving the tolerance of plants for various stresses especially, high temperature, low temperature, salinity as well as drought and so on.

E] Improvement of Multiple Stress Tolerance of Crop Plants—Use of Hybrid-Type Histidine Kinase Gene Isolated from Rice IR 64 in Improvement of Multiple Stress Tolerance of Crop Plants:—

To establish that the presently provided gene—OsHk3b is capable of improving stress, particularly the abiotic stress tolerance in plants [transgenic rice], the IR64 plant is transformed with gene—OsHK3b under the control of judicially selected constitutive promoter using pCAMBIA1304-OsHk3b, and to have a comparison, the IR 64 plant is also transformed with vector control (VC having no OsHk3b gene).

In accordance with the present invention, the transformation of IR64 is achieved by surface sterilizing the seeds of IR-64 (FIG. 6a) and transferring on the callus induction media for callus formation, the grown callus (FIG. 6b) is further sub-cultured and again kept on the callus induction media for about 5-7 days (FIG. 6c), these calli are co-infected with Agrobacterium strain LBA4404, containing pCAM-BIA1304-OsHk3b (FIG. 6d), the co-infected rice calli is further kept for co-cultivation for about 2-3 days (FIG. 6e), the overgrown Agrobacterium (on rice calli) is washed with antibiotic—cefotaxim (FIG. 6f, the washed callus is then transferred on a selection plate for growth of the transformed calli (FIG. 6g), the transformed calli is further kept on the regeneration media (FIG. 6h) and sub-cultured on fresh regeneration media (FIG. 6i), the completely regenerated plant is transferred into culture tubes for hardening (FIG. 6j), then the hardened plant is further transferred into earthen pots and kept in a green house to develop complete transgenic IR64 plants (FIG. 6k).

To establish the possible role of gene—OsHk3b in improving stress tolerance in rice, leaf disc assay analysis is performed. In this analysis, the discs of leaf are cut from the various plants and incubated in solution containing high salinity (200 mM NaCl), and also a control is developed where instead of salt, normal water is added. After about 96 h of incubation, comparison of the discs is done and their general viability is looked for (FIG. 7A), the estimation of chlorophyll for these samples is also carried out and the results are presented in FIG. 7B. This analysis indicates that the transgenic IR64 plants (over expressing OsHk3b) shows relatively less bleaching even under control conditions (without salinity stress) in T9 (FIG. 7A5 T29 (FIG. 7A7) as compared to the non-transformed IR64 i.e., WT (FIG. 7A1) and VC (FIG. 7A3). Similarly, more retention of chlorophyll in IR64 transgenic plants T9 (FIG. 7B6) and T23 (FIG. 7B8) is also observed than its non-transgenic counterparts, WT (FIG. 7B2) and VC (FIG. 7B4) under the salinity stress confirming that overexpression of gene—OsHk3b in transgenic rice plants enables them to survive better under abiotic stress especially salinity.

F] Confirmation of OsHk3b Transgenic Rice Plants:—

To confirm the integration of OsHk3b gene into the genome of IR64 overexpression lines, tissue PCR was done using gene—OsHk3b specific forward primer and vector (pCAMBIA1304) specific reverse primer. The amplification show a band of 1.4 kb size in lane number 4, 7, 8, 9, 10, 11, 18, 19, 23, 32 indicates the successful integration of OsHk3b transgene into the genome of these IR64 transgenic plants (FIG. 8).

G] Transgenic Lines of Rice ($T_1$) Show Tolerance Towards Salinity Stress During Seed Germination:—

Seeds of wild type IR64 (WT) and overexpression OsHk3b were kept in petridish containing cotton saturated with ½ Yoshida containing 200 mM NaCl (salinity stress). The inventors have surprisingly found that the germination rate of seeds on 200 mM NaCl is more in case of overexpression OsHk3b lines in comparison to the wild type seeds (FIG. 2A). When length of root and shoot of germinated seedlings were measured after fourth days of growth, inventors surprisingly found that both root and shoot length was more in overexpression lines, but less in the wild type (FIG. 2B). To determine the available $K^+$ and $Na^+$ ions in the transgenic plants, inventors have estimated the amount of available ions by flame photometer and found that overexpressing transgenic plants retain more $K^+/Na^+$ ratio than the wild type plants (FIG. 2C). This analysis indicates that OsHk3b overexpression in rice provide salinity stress tolerance to germinating seeds.

H] Transgenic Seedlings Overexpressing OsHk3b are Better Adapted to Salinity Stress as Compared to WT:

Transgenic rice seedlings (T1) were further used for testing the tolerance towards salinity. Seven days old seedlings were transferred into 200 mM NaCl containing half Yoshida medium, whereas seedlings grown in ½ Yoshida medium without NaCl was used as control. Photographs were taken after ten days of stress. Inventors found that overexpression OsHk3b overexprssing plants were surprisingly able to withstand more salinity stress (FIG. 3B) and retain more chlorophyll (FIG. 3C) than the wild type plant under salinity stress condition. Even under non-stress conditions, the growth of OsHk3b overexpression plants was found to be more than that of wild type lines of OsHK3b (FIG. 3A). This analysis further indicated that OsHk3b overexpression in rice provide salinity stress tolerance to seedlings.

THE DETAILED LEGENDS OF THE ACCOMPANYING FIGURES

FIG. 1A: Primer sequences used for the isolation of OsHk3b gene

FIG. 1B: Conditions for Polymerase Chain Reaction (PCR)

FIG. 1C: Agarose gel electrophoresis of polymerase chain reaction product showing an amplification product of size 2.6 Kb (precisely 2598 bp) of OsHk3b FIG. 2A: The complete Gene sequence of ORF of OsHk3b which is 2598 bp (submitted to NCBI under GenBank accession number Bankit 1121378 FJ004641).

FIG. 2B: The complete deduced amino acid sequence for protein encoded by ORF of OsHk3b which is 95.9 kDa. Transmitter domain has a conserved Histidine residue at 291 position (H, shown in red). Receiver domain has a conserved Aspartate residue at position 771 (D, shown in blue). The sequence has been submitted to NCBI under GenBank accession number Bankit 1121378 FJ004641).

FIG. 3A: Confirmation of cloning of OsHk3b into pYES2 vector: Restriction digestion of pYES2-OsHk3b plasmid with SphI to confirm the orientation of OsHK3b ORF; M: 1 kb DNA ladder; 1,2,3,4 and 5 are pYES2-OsHK3b plasmid; 6: pYES2 and 7: undigested pYES2–OsHk3b plasmid. Schematic representation of pYES2-OsHk3b has been shown on the top of figure.

FIG. 3B: Confirmation of cloning of OsHk3b into pCAMBIA1304 vector: Restriction digestion of pCAMBIA1304-OsHK3b plasmid with SphI to confirm the orientation of OsHk3b ORF; M: 1 kb DNA ladder; 1,2,3 and 4: pCAMBIA1304-OsHK3b plasmid; 5: pCAMBIA1304 and 6: undigested pCAMBIA1304-OsHK3b plasmid. Schematic representation of pCAMBIA1304-OsHk3b has been shown on the top of figure.

Figure 4:
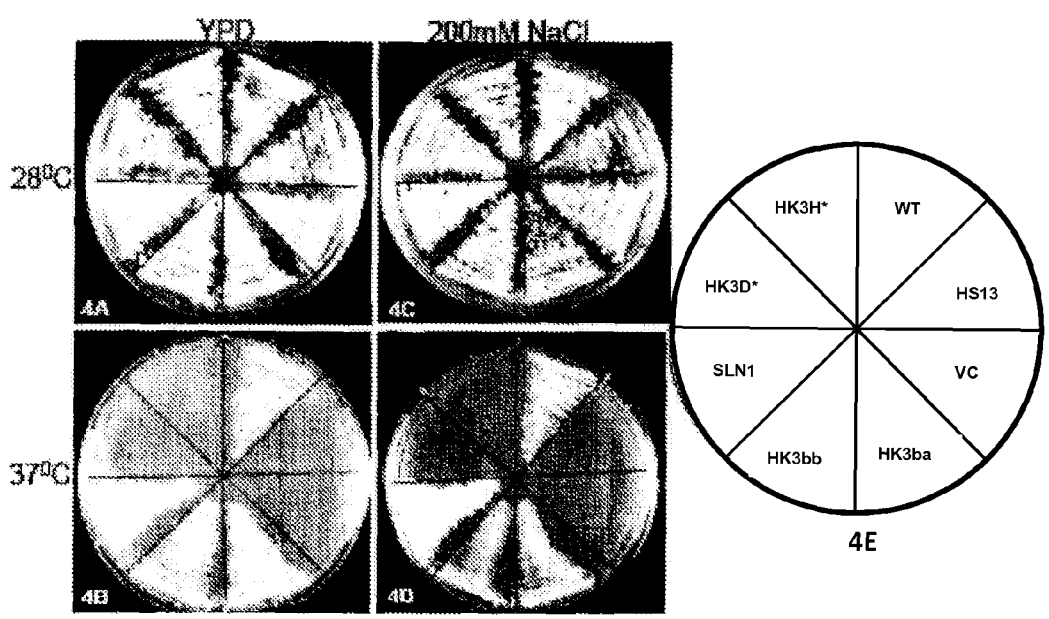
FIG. 4 illustrates functional complementation of yeast SLN1-temperature dependent osmosensitive mutant HS13 by the rice OsHK3b ORF in accordance with the most preferred embodiment of the present invention.

FIG. 4: Functional complementation of yeast SLN1-temperature sensitive osmosensing mutant HS13 by the rice OsHK3b ORF. Complementation of the mutation by expression of OSHK3B ORF; Sensitivity of yeast strains cultured at 28° C., 37° C. for three days on normal YPD media and YPD with 200 mM NaCl (saline medium).

Strains used in this experiment:
WT, wild-type yeast;
HS13, sln1-ts mutant;
VC, HS13 carrying vector (pYES2) only;
OSHK3a and OSHK3b, HS13 carrying expression pYES2-OsHK3b;
SLN1, HS13 carrying wild type expression sln1 allele;
HK3H*, HS13 carrying histidine mutated pYES2-OsHK3b (OsHK3H291V) and
HK3D*, HS13 carrying aspartate mutated pYES2-OsHK3b (OsHK3D772E)
4A: Incubation of different yeast strains on YPD medium at 28° C.
4B: Incubation of different yeast strains on YPD medium at 28° C.
4C: Incubation of different yeast strains on salinity stress (YPD containing 200 mM NaCl) medium at 28° C.;
4D: Incubation of different yeast strains on salinity stress (YPD containing 200 mM NaCl) medium at 28° C.;
4E: Schematic representation of different yeast strains used for streaking in 4A, 4B, 4C and 4D.

Figure 5:
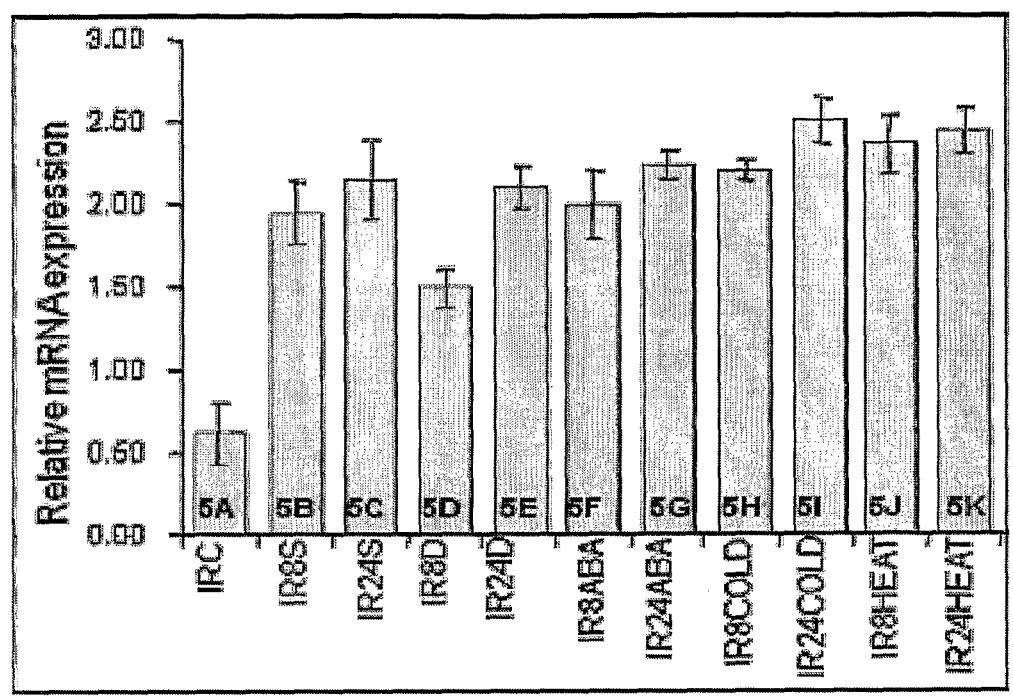
FIG. 5 illustrates the histogram showing the inducibility of OsHK3b by various abiotic stresses in rice in accordance with the most preferred embodiment of the present invention.

FIG. 5: The histogram showing the inducibility of OsHK3b by various abiotic stresses in rice. X axis has different samples; Y axis shows relative mRNA expression. qRT-PCR analysis was performed using cDNA synthesized from mRNA of IR64 (IR) under S (200 mM NaCl), D (dehydration), ABA (100 uM Abscisic acid), Heat (42° C.) and Cold (4° C.) at 8 (hrs) and 24 (24 hrs) of stress along with C (control) samples.

FIG. 6: *Oryza sativa* Cv IR64 transformation and regeneration. a. Seeds of Rice IR-64; b. Rice callus formation on callus induction media; c. sub-cultured rice callus kept on callus induction media for 5-7 days; d. co-infection of rice calli with *Agrobacterium* strain LBA4404 containing pCAMBIA1304-OsHK3b construct; e. co-cultivation of co-infected rice calli; f. washing of overgrown *Agrobacterium* with Antibiotic cefotaxim; g. Transfer of washed callus on selection plate; h. transformed callus was kept on regeneration medium; I. regenerated plantlets was transferred on fresh regeneration medium; j. completely regenerated plant was transferred into culture tubes for hardening; k. plant from step j is further transferred into earthen pot and kept in green house FIG. 7A: Leaf Disc assay. Showing the bleaching rate of different leaf samples under control and salinity stress.

FIG. 7B: Total Chlorophyll content. X axis: different samples, Y: axis total chlorophyll content in μg per gram fresh weight of leaves
WT, IR64
VC, IR64 transformed with vector without OsHK3b gene;
T9, IR64 transformed with vector with OsHK3b gene (plant number 9);
T23, IR64 transformed with vector with OsHK3b gene (plant number 23).

FIG. 8: illustrates confirmation of IR64-OsHk3b regenerated plants by tissue PCR. (A) PCR amplification was done using the tissue of regenerated plantlets as template and vector specific forward and gene specific reverse primers. M: DNA marker; 4, 7, 8, 9, 10, 11, 12, 18, 19, 23, 32 are the different OsHk3b transgenic plantlets used for tissue PCR, IR: non-transformed IR64 i.e. wild type plants and +ve: pCAMBIA-OsHk3b used as template.

FIG. 9: illustrates confirmation of multiple stress tolerance by germination test for IR64-OsHk3b transgenic seeds ($T_1$) in presence of 200 mM NaCl. (A) Seeds of WT: Wild type; OE1: overexpressing OsHK3b line, were kept in 200 mM NaCl containing ½ Yoshida media; (B) Measurement of shoot length; (C) Measurement of root length; (E) Measurement of $K^+/Na^+$ ratio. Data was taken after 96 h of salinity stress.

FIG. 10: illustrates growth of IR64-OsHk3b transgenic seedlings ($T_1$) under control (without salinity) and Salinity stress condition and their chlorophyll measurement. (A) in normal ½ Yoshida media (B) in NaCl (200 mM) supplemented ½ Yoshida media. WT: wild type IR64, OE1: overexpressing OsHK3b line. (C) Chlorophyll measurement from control salinity stressed seedlings. 7 days old seedlings grown under control conditions were subjected to salinity stress (200 mM NaCl) for 10 days after the photograph was taken.

The invention claimed is:

1. A method for cloning a hybrid-type histidine kinase gene into a recombinant plasmid, comprising the steps of:
   (i) isolating cDNA from rice cv IR64;
   (ii) providing a polymerase chain reaction mixture comprising:
      a) said isolated cDNA of the rice cv IR64; and
      b) a forward primer consisting of SEQ ID NO: 1; and
      c) a reverse primer consisting of SEQ ID NO: 2;
   (iii) performing a polymerase chain reaction (PCR) using the mixture of step (ii) to produce an amplified hybrid-type histidine kinase (OsHK3b) gene consisting of SEQ ID NO: 3 of the rice cv IR64 cDNA; and
   (iv) cloning the amplified (OsHK3b) gene of step (iii) into the recombinant plasmid, wherein in said PCR, the step of annealing is performed at about 55° C.

2. The method as claimed in claim 1, wherein isolating said cDNA from rice cv IR64 comprises the steps of:
   a) isolating total RNA from a salinity stressed leaf tissue of the rice cv IR64;
   b) isolating mRNA from the total RNA by employing streptavidin paramagnetic beads and biotin-labeled oligo d(T)$_{20}$ primer; and
   c) synthesizing a first strand cDNA from the mRNA.

3. The method as claimed in claim 1, wherein performing said polymerase chain reaction (PCR) comprises the steps of:
   i) performing an initial denaturation of the PCR reaction mixture at about 94° C. for about 5 min;
   ii) performing a denaturation of the reaction mixture from step—i) at about 94° C. for about 1 min;
   iii) performing an annealing of the reaction mixture from step—ii) at about 55° C. for about 1 min;
   iv) performing an extension of the reaction mixture from step—iii) at about 72° C. for about 3 min; and
   v) performing a final extension of the reaction mixture from step—iv) at about 72° C. for about 7 min;
   wherein the denaturation, the annealing, and the extension steps are repeated for about 34 cycles.

4. A method for cloning a hybrid-type histidine kinase (OsHk3b) gene into a yeast expression vector, comprising the steps of:
   (i) isolating cDNA from rice cv IR64;
   (ii) providing a polymerase chain reaction mixture comprising:
      a) said isolated cDNA of the rice cv IR64; and
      b) a forward primer consisting of SEQ ID NO: 1; and
      c) a reverse primer consisting of SEQ ID NO: 2;
   (iii) performing a polymerase chain reaction using the mixture of step (ii) to produce an amplified hybrid-type histidine kinase (OsHK3b) gene consisting of SEQ ID NO: 3 of the rice cv IR64 cDNA;
   (iv) cloning the amplified (OsHK3b) gene of step (iii) into a recombinant plasmid,
   (v) amplifying by a polymerase chain reaction (PCR), the cloned amplified (OsHk3b) gene of step (iv) from the plasmid by treating the plasmid with a forward primer OsHk3bSpeIF and a reverse primer OsHk3bSpeJR to produce an amplified OsHk3b gene fragment; and
   (vi) cloning the amplified OsHk3b gene fragment containing the complete open reading frame of the OsHk3b gene along with additional Spa sites into the yeast expression vector;
   wherein in said PCR reactions, the step of annealing is performed at about 55° C.

5. The method as claimed in claim 4, wherein the polymerase chain reaction to amplify the OsHk3b gene of step (v) comprises the steps of:
   i) performing an initial denaturation of the reaction mixture comprising the forward primer OsHk3bSpeIF, the reverse primer OsHk3bSpeIR and the plasmid of the OsHk3b gene consisting of SEQ ID NO: 3 at about 94° C. for about 5 min;
   ii) performing a denaturation of the reaction mixture from step—i) at about 94° C. for about 1 min;
   iii) performing an annealing of the reaction mixture from step—ii) at about 55° C. for about 1 min;
   iv) performing an extension of the reaction mixture from step—iii) at about 72° C. for about 3 min; and
   v) performing a final extension of the reaction mixture from step—iv) at about 72° C. for about 7 min;
   wherein the denaturation, the annealing, and the extension steps are repeated for about 34 cycles.

6. An isolated yeast expression vector comprising SEQ ID NO: 3.

7. A method for cloning a hybrid-type histidine kinase (OsHk3b) gene into a plant expression vector, comprising the steps of:
(i) isolating cDNA from rice cv IR64;
(ii) providing a polymerase chain reaction mixture comprising:
   a) said isolated cDNA of the rice cv IR64; and
   b) a forward primer consisting of SEQ ID NO: 1; and
   c) a reverse primer consisting of SEQ ID NO: 2;
(iii) performing a polymerase chain reaction using the mixture of step (ii) to produce an amplified hybrid-type histidine kinase (OsHK3b) gene consisting of SEQ ID NO: 3 of the rice cv IR64 cDNA;
(iv) cloning the amplified (OsHK3b) gene of step (iii) into a recombinant plasmid,
(v) amplifying by a polymerase chain reaction (PCR), the cloned amplified (OsHk3b) gene from the plasmid by treating the plasmid with a forward primer OsHk3bSpeIF and a reverse primer OsHk3bSpeJR to produce an amplified OsHk3b gene fragment; and
(vi) cloning the amplified OsHk3b gene fragment containing the complete open reading frame of the OsHk3b gene along with additional Spa sites into the plant expression vector; wherein in said PCR reactions, the step of annealing is performed at about 55° C.

8. The method as claimed in claim 7, wherein said polymerase chain reaction to amplify the OsHk3b gene of step (v) comprises the steps of:
i) performing an initial denaturation of the reaction mixture comprising the forward primer OsHk3bSpeJF, the reverse primer OsHk3bSpeIR and the plasmid of the OsHk3b gene consisting of SEQ ID NO: 3 at about 94° C. for about 5 min;
ii) performing a denaturation of the reaction mixture from step—i) at about 94° C. for about 1 min;
iii) performing an annealing of the reaction mixture from step—ii) at about 55° C. for about 1 min;
iv) performing an extension of the reaction mixture from step—iii) at about 72° C. for about 3 min; and
v) performing a final extension of the reaction mixture from step—iv) at about 72° C. for about 7 min;
wherein the denaturation, the annealing, and the extension steps are repeated for about 34 cycles.

9. An isolated plant expression vector comprising SEQ ID NO: 3.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial
<220> FEATURE:
<223> OTHER INFORMATION: Primer OSHkb3F

<400> SEQUENCE: 1
atgacgttcg cgaggtacgc                                           20

<210> SEQ ID NO 2
<211> LENGTH: 24
<212> TYPE: DNA
<213> ORGANISM: Artificial
<220> FEATURE:
<223> OTHER INFORMATION: primer OsHkb3R

<400> SEQUENCE: 2
ctattcaact tggtcatgat tttg                                      24

<210> SEQ ID NO 3
<211> LENGTH: 2598
<212> TYPE: DNA
<213> ORGANISM: Oryza sativa

<400> SEQUENCE: 3
atgacgttcg cgaggtacgc ggtgaggacg gcgttcgagc ggccgctgac gagcggggtg    60
gcgtacgcgg tgcgggtgac gcacggcgag cgggagcatt tcgagcggca gcaggggtgg   120
acgatcaaga agatgtactc ctcctccaac aagaagcagt cgtcgtcggg gccggggccg   180
ggggacgccg ccgtcgcgga gatccgggag cccgccgagg agtacgcccc ggtcatcttc   240
gcccaggacg cctacaagca cgtcatctcc ttcgacatgc tctccgggaa tgaggatcgg   300
aaaaacatac tatactctag gaaatctggc aagggtgtcc tgactgctcc tttcaagcta   360
ctgaataatc gcctcggagt aatctcgaca tacactgttt ataagtctga gctccctgca   420
aatgccaggc cacatgaacg catccaagcc gcgattggct atttgggcgg catatttgac   480
atacaagcac tcgtcgaaaa gttgctcaaa caactcgcga gccaggaatc catcatggtg   540
aatgtgtatg atacgaccaa cgagaacccg atcagtatgt acggtgatga tactgggagt   600
ggcatgtgcc atgtcagcgt gctcaacttt ggtgatccat cgagaaagca tgagatgcat   660
tgcaggttcg aaaaaaagcc accatggcca tggctggcaa taacgtcatc gtttggaact   720
cttgtgattg ctttactgac tggtcacata tttcaagcta ctgtccatcg gattgctaaa   780
gttgaagatg atttccacaa gatgagcgaa ctcaagaagc gtgcagaaga tgcagacgtc   840
gcaaagtcac agttcttggc tactgtttca catgagatca gaactccaat gaatggtgtt   900
ctagggatgc tccaaatgct catggatact gatttggaca cgacgcagca ggactatgtt   960
agaactgccc aagctagtgg aaaagctttg gtctctctca tcaatgaggt tcttgatcag  1020
gcaaagattg agtctggtaa acttgagctc gagacggtgc cctttgatct agaacagtt   1080 tgtgacgaca ttttatctct gttttgtggg aaagctcagg agaaggact ggagttagca   1140 gtgtatgtct cggatcaagt tccacagata cttattggcg atcctggcag gataagacaa  1200
atcattacga atcttgtcgg gaactccata aagttcacag agagagggca tatatacctg  1260
acagttcatg tagttgaaga ggtcatgagt tgtttggagg tagagacagg aattcagaac  1320
acaaacactt taagtggcta tccagtagcc aacagaagat gtagctggga gagcattcgg  1380

```
cttttcaaca gagaattaca ctcatctgag aagtcttttg cgcccatcgc atctgattca    1440
ataagcttgg ttatatctgt tgaagatact ggcgtcggca tcccatttga agcccaatcc    1500
cgtgtgttca cccctttcat gcaggtaggt ccatccattg cccgcatcca tgggggcact    1560
ggcattggat taagcatcag caagtgcttg gttggtctca tgaagggaga aatcggtttt    1620
gcaagtaagc cccatgttgg ttctactttc accttcaccg cggtgcttat gagggcacac    1680
tgcaaaggaa atgacatcaa atcatcagaa tttaaaggga tcaatgcatt ggttgttgat    1740
cataggccag tccgtgcaaa ggttaccaag tatcacttgc aaagacttgg agttaagacc    1800
gaactgacag ctgagctaaa tcagttcatt tctaaattaa actctggatc actgactgca    1860
aagctagtgc taatagacaa ggaaacctgg cttaaggaat cccattgcac gcctcttctg    1920
gttaacaaat tgaggaataa tgacaagcca gactctccta agttatttct tttggggagc    1980
tctgcaagtt ctcccaaggg cggttcagat acatccaggg aacataactt gaatgtaata    2040
atgaagccgc ttcgtgcaag catgcttcag gtctcactac gacgagcact aggtggggtc    2100
gataaggtgc actgcaggaa tggagtagtt ggcaattcaa cattgggcag ccttcttcac    2160
aagaagcaaa tcattgttgt cgacgacaat atcgttaacc tgaaggtggc tggtgctctt    2220
aagaagtatg gtgccgaagt tacttgtgca gacagcggga aaaaagcaat cacattgcta    2280
aaacccccgc acaattttga tgcttgtttc atggacatac agatgccaga aatggatggg    2340
tttgaagcca ctagaaggat tagagtgatg gaaagagatc taaatgagcg aatagaacgc    2400
ggagaggcgc caccagaatg tgctagtatt cagaggtggc gaactcctat attggcgatg    2460
acggcggatg ttatacaggc aacacacgag gagtgcctga aaagcgaaat ggatggctat    2520
gtctccaagc catttgaagg ggagcagctg tacagcgaag tagcgcggtt tttccaaaat    2580
catgaccaag ttgaatag                                                  2598
```

```
<210> SEQ ID NO 4
<211> LENGTH: 865
<212> TYPE: PRT
<213> ORGANISM: Oryza sativa

<400> SEQUENCE: 4

Met Thr Phe Ala Arg Tyr Ala Val Arg Thr Ala Phe Glu Arg Pro Leu
1               5                   10                  15

Thr Ser Gly Val Ala Tyr Ala Val Arg Val Thr His Gly Glu Arg Glu
            20                  25                  30

His Phe Glu Arg Gln Gln Gly Trp Thr Ile Lys Lys Met Tyr Ser Ser
        35                  40                  45

Ser Asn Lys Lys Gln Ser Ser Ser Gly Pro Gly Pro Gly Asp Ala Ala
    50                  55                  60

Val Ala Glu Ile Arg Glu Pro Ala Glu Glu Tyr Ala Pro Val Ile Phe
65                  70                  75                  80

Ala Gln Asp Ala Tyr Lys His Val Ile Ser Phe Asp Met Leu Ser Gly
                85                  90                  95

Asn Glu Asp Arg Lys Asn Ile Leu Tyr Ser Arg Lys Ser Gly Lys Gly
            100                 105                 110

Val Leu Thr Ala Pro Phe Lys Leu Leu Asn Asn Arg Leu Gly Val Ile
        115                 120                 125

Ser Thr Tyr Thr Val Tyr Lys Ser Glu Leu Pro Ala Asn Ala Arg Pro
    130                 135                 140

His Glu Arg Ile Gln Ala Ala Ile Gly Tyr Leu Gly Gly Ile Phe Asp
145                 150                 155                 160
```

-continued

```
Ile Gln Ala Leu Val Glu Lys Leu Leu Lys Gln Leu Ala Ser Gln Glu
                165                 170                 175
Ser Ile Met Val Asn Val Tyr Asp Thr Thr Asn Glu Asn Pro Ile Ser
            180                 185                 190
Met Tyr Gly Asp Asp Thr Gly Ser Gly Met Cys His Val Ser Val Leu
        195                 200                 205
Asn Phe Gly Asp Pro Ser Arg Lys His Glu Met His Cys Arg Phe Glu
    210                 215                 220
Lys Lys Pro Pro Trp Pro Trp Leu Ala Ile Thr Ser Ser Phe Gly Thr
225                 230                 235                 240
Leu Val Ile Ala Leu Leu Thr Gly His Ile Phe Gln Ala Thr Val His
                245                 250                 255
Arg Ile Ala Lys Val Glu Asp Asp Phe His Lys Met Ser Glu Leu Lys
                260                 265                 270
Lys Arg Ala Glu Asp Ala Asp Val Ala Lys Ser Gln Phe Leu Ala Thr
            275                 280                 285
Val Ser His Glu Ile Arg Thr Pro Met Asn Gly Val Leu Gly Met Leu
        290                 295                 300
Gln Met Leu Met Asp Thr Asp Leu Asp Thr Thr Gln Gln Asp Tyr Val
305                 310                 315                 320
Arg Thr Ala Gln Ala Ser Gly Lys Ala Leu Val Ser Leu Ile Asn Glu
                325                 330                 335
Val Leu Asp Gln Ala Lys Ile Glu Ser Gly Lys Leu Glu Leu Glu Thr
            340                 345                 350
Val Pro Phe Asp Leu Arg Thr Val Cys Asp Asp Ile Leu Ser Leu Phe
        355                 360                 365
Cys Gly Lys Ala Gln Glu Lys Gly Leu Glu Leu Ala Val Tyr Val Ser
    370                 375                 380
Asp Gln Val Pro Gln Ile Leu Ile Gly Asp Pro Gly Arg Ile Arg Gln
385                 390                 395                 400
Ile Ile Thr Asn Leu Val Gly Asn Ser Ile Lys Phe Thr Glu Arg Gly
                405                 410                 415
His Ile Tyr Leu Thr Val His Val Glu Glu Val Met Ser Cys Leu
            420                 425                 430
Glu Val Glu Thr Gly Ile Gln Asn Thr Asn Thr Leu Ser Gly Tyr Pro
        435                 440                 445
Val Ala Asn Arg Arg Cys Ser Trp Glu Ser Ile Arg Leu Phe Asn Arg
    450                 455                 460
Glu Leu His Ser Ser Glu Lys Ser Phe Ala Pro Ile Ala Ser Asp Ser
465                 470                 475                 480
Ile Ser Leu Val Ile Ser Val Glu Asp Thr Gly Val Gly Ile Pro Phe
                485                 490                 495
Glu Ala Gln Ser Arg Val Phe Thr Pro Phe Met Gln Val Gly Pro Ser
            500                 505                 510
Ile Ala Arg Ile His Gly Gly Thr Gly Ile Gly Leu Ser Ile Ser Lys
        515                 520                 525
Cys Leu Val Gly Leu Met Lys Gly Glu Ile Gly Phe Ala Ser Lys Pro
    530                 535                 540
His Val Gly Ser Thr Phe Thr Phe Thr Ala Val Leu Met Arg Ala His
545                 550                 555                 560
Cys Lys Gly Asn Asp Ile Lys Ser Ser Glu Phe Lys Gly Ile Asn Ala
                565                 570                 575
```

-continued

| | | | | | | | | | | | |
|---|---|---|---|---|---|---|---|---|---|---|---|
|Leu|Val|Val|Asp 580|His|Arg|Pro|Val|Arg 585|Ala|Lys|Val|Thr|Lys 590|Tyr|His|

Leu Val Val Asp His Arg Pro Val Arg Ala Lys Val Thr Lys Tyr His
            580                 585                 590

Leu Gln Arg Leu Gly Val Lys Thr Glu Leu Thr Ala Glu Leu Asn Gln
        595                 600                 605

Phe Ile Ser Lys Leu Asn Ser Gly Ser Leu Thr Ala Lys Leu Val Leu
        610                 615                 620

Ile Asp Lys Glu Thr Trp Leu Lys Glu Ser His Cys Thr Pro Leu Leu
625                 630                 635                 640

Val Asn Lys Leu Arg Asn Asn Asp Lys Pro Asp Ser Pro Lys Leu Phe
                645                 650                 655

Leu Leu Gly Ser Ser Ala Ser Ser Pro Lys Gly Gly Ser Asp Thr Ser
            660                 665                 670

Arg Glu His Asn Leu Asn Val Ile Met Lys Pro Leu Arg Ala Ser Met
        675                 680                 685

Leu Gln Val Ser Leu Arg Arg Ala Leu Gly Val Asp Lys Val His
        690                 695                 700

Cys Arg Asn Gly Val Val Gly Asn Ser Thr Leu Gly Ser Leu Leu His
705                 710                 715                 720

Lys Lys Gln Ile Ile Val Asp Asp Asn Ile Val Asn Leu Lys Val
                725                 730                 735

Ala Gly Ala Leu Lys Lys Tyr Gly Ala Glu Val Thr Cys Ala Asp Ser
            740                 745                 750

Gly Lys Lys Ala Ile Thr Leu Leu Lys Pro Pro His Asn Phe Asp Ala
        755                 760                 765

Cys Phe Met Asp Ile Gln Met Pro Glu Met Asp Gly Phe Glu Ala Thr
770                 775                 780

Arg Arg Ile Arg Val Met Glu Arg Asp Leu Asn Glu Arg Ile Glu Arg
785                 790                 795                 800

Gly Glu Ala Pro Pro Glu Cys Ala Ser Ile Gln Arg Trp Arg Thr Pro
                805                 810                 815

Ile Leu Ala Met Thr Ala Asp Val Ile Gln Ala Thr His Glu Glu Cys
            820                 825                 830

Leu Lys Ser Glu Met Asp Gly Tyr Val Ser Lys Pro Phe Glu Gly Glu
        835                 840                 845

Gln Leu Tyr Ser Glu Val Ala Arg Phe Phe Gln Asn His Asp Gln Val
        850                 855                 860

Glu
865

<210> SEQ ID NO 5
<211> LENGTH: 29
<212> TYPE: DNA
<213> ORGANISM: Artificial
<220> FEATURE:
<223> OTHER INFORMATION: OSHKb3HisMUTF

<400> SEQUENCE: 5
ggctactgtt tcagttgaga tcagaactc                                    29

<210> SEQ ID NO 6
<211> LENGTH: 28
<212> TYPE: DNA
<213> ORGANISM: Artificial
<220> FEATURE:
<223> OTHER INFORMATION: OSHKb3HisMUTR

```
<400> SEQUENCE: 6
agttctgatc tcaactgaaa cagtagcc                                        28

<210> SEQ ID NO 7
<211> LENGTH: 31
<212> TYPE: DNA
<213> ORGANISM: Artificial
<220> FEATURE:
<223> OTHER INFORMATION: OSHKb3AspMUTF

<400> SEQUENCE: 7
gatgcttgtt tcatgctcat acagatgcca g                                    31

<210> SEQ ID NO 8
<211> LENGTH: 31
<212> TYPE: DNA
<213> ORGANISM: Artificial
<220> FEATURE:
<223> OTHER INFORMATION: OSHKb3AspMUTR

<400> SEQUENCE: 8
ctggcatctg tatgagcatg aaacaagcat c                                    31
```